(12) United States Patent
Cousins et al.

(10) Patent No.: US 12,221,447 B2
(45) Date of Patent: Feb. 11, 2025

(54) METHODS AND COMPOSITIONS FOR DRUGS TO TREAT OPHTHALMIC DISEASES

(71) Applicant: Duke University, Durham, NC (US)

(72) Inventors: Scott W. Cousins, Durham, NC (US); Priyatham S. Mettu, Durham, NC (US); David M. Gooden, Durham, NC (US)

(73) Assignee: Duke University, Durham, NC (US)

( * ) Notice: Subject to any disclaimer, the term of this patent is extended or adjusted under 35 U.S.C. 154(b) by 919 days.

(21) Appl. No.: 17/269,830

(22) PCT Filed: Aug. 20, 2019

(86) PCT No.: PCT/US2019/047309
§ 371 (c)(1),
(2) Date: Feb. 19, 2021

(87) PCT Pub. No.: WO2020/041344
PCT Pub. Date: Feb. 27, 2020

(65) Prior Publication Data
US 2021/0198266 A1  Jul. 1, 2021

Related U.S. Application Data

(60) Provisional application No. 62/719,938, filed on Aug. 20, 2018.

(51) Int. Cl.
| | | |
|---|---|---|
| C07D 487/04 | (2006.01) | |
| A61P 27/02 | (2006.01) | |
| A61P 37/06 | (2006.01) | |
| C07D 471/06 | (2006.01) | |

(52) U.S. Cl.
CPC ............ *C07D 487/04* (2013.01); *A61P 27/02* (2018.01); *A61P 37/06* (2018.01); *C07D 471/06* (2013.01)

(58) Field of Classification Search
CPC ..... C07D 487/04; C07D 471/06; A61P 27/02; A61P 37/06
See application file for complete search history.

(56) References Cited

U.S. PATENT DOCUMENTS

| 8,207,185 B2 | 6/2012 | Means |
|---|---|---|
| 9,733,406 B2 * | 8/2017 | Doutova ............... G02B 5/305 |

FOREIGN PATENT DOCUMENTS

| JP | 2003012516 A | 1/2003 |
|---|---|---|
| NO | 2007080420 A1 | 7/2007 |
| WO | 2008045273 A2 | 4/2008 |
| WO | 2012024255 A2 | 2/2012 |
| WO | 2020041344 A1 | 2/2020 |

OTHER PUBLICATIONS

Mai et al. Chem Commun 2018 54 pp. 10240-10243 (Year: 2018).*
Tokumitsu et al. ((2002), STO-609, a Specific Inhibitor of the Ca2+/Calmodulin-dependent Protein Kinase Kinase, Journal of Biological Chemistry, 18, 15813-15818 (Year: 2002).*
"Derivative." Merriam-Webster.com Dictionary, Merriam-Webster, https://www.merriam-webster.com/dictionary/derivative. Accessed Mar. 27, 2024. (Year: 2024).*
Office Action dated Feb. 26, 2023 for associated Chinese patent application No. 201980054524X (6 pages).
Examination Report dated May 9, 2023 for associated European patent application No. 19852526.3 (12 pages).
Office Action dated Jul. 26, 2023 for associated Mexican Patent Application No. MX/a/2021/002028 (8 pages).
Office Action dated Jul. 31, 2023 for associated Israeli Patent Application No. 280,952 (5 pages).
Notification of Reasons for Refusal dated Aug. 22, 2023 for associated Japanese Patent Application No. 2021-509910 (10 pages).
PubChem-CID-6618466, Create Date: Jun. 5, 2006 (Jun. 5, 2006)(9 pages).
PubChem-CID-91522194, Create Date: Mar. 17, 2015 (Mar. 17, 2015) (6 pages).
Notification of Transmittal and International Search Report and Written Opinion issued Dec. 23, 2019, for related application PCT/US19/47039 (thirty-five (35) pages).
Laying Open Patent Gazette by the Intellectual Property Office on Jun. 16, 2020, under Laying Open No. 202021968 for related ROC (Taiwan) Pat. Appln. No. 108129703 (two (2) pages).
Anderson, K., et al. "Hypothalamic CaMKK2 Contributes to the Regulation of Energy Balance." Cell Metabolism, May 2008, 377-388, 7, Elsevier Inc., Amsterdam.

(Continued)

*Primary Examiner* — Juliet C Switzer
*Assistant Examiner* — Dawanna Shar-Day White
(74) *Attorney, Agent, or Firm* — Olive Law Group PLLC; Nathan P. Letts

(57) ABSTRACT

The presently disclosed subject matter is directed to compositions and methods for treating CaMKK2-mediated ophthalmic diseases, including but not limited to 1) ocular surface inflammatory diseases (OSIDs), including but not limited to ocular graft versus host disease, ocular cicatricial pemphigoid, vernal keratoconjunctivitis, allergic eye disease, meibomian gland dysfunction, aqueous tear deficiency (common dry eye disease), corneal scarring, and conjunctival scarring and fibrosis; 2) uveitis and other inflammatory diseases of the eye, including but not limited to keratitis, scleritis, iritis, iridocyclitis, intermediate uveitis, pars planitis, posterior uveitis, choroiditis, chorioretinitis, retinitis, or panuveitis of noninfectious, infectious, or idiopathic etiologies; and 3) "back of the eye" retinal diseases, which include dry age-related macular degeneration, neovascular age-related macular degeneration, diabetic retinopathy, retinal vascular diseases (e.g. retinal vein occlusion, retinal artery occlusion), and retinal degenerations and dystrophies, in a subject. Particularly, the disclosed compounds exhibit improvements over STO-609, a well characterized specific inhibitor of CaMKK2. The disclosed compounds exhibit enhanced aqueous solubility and formulation, as well as elimination of non-binding isomers during production. The disclosed inhibitor compounds can be used to effectively treat ophthalmic diseases, cancers, appetite disorders, systemic inflammatory diseases, and the like.

18 Claims, 10 Drawing Sheets

(56) References Cited

OTHER PUBLICATIONS

Espinosa-Heidmann, D., et al. "Bone Marrow Transplantation Transfers Age-Related Susceptibility to Neovascular Remodeling in Murine Laser-Induced Choroidal Neovascularization." Investigative Ophthalmology and Visual Science (IOVS), Nov. 2013, 7439-7449, 54(12), Association for Research in Vision and Ophthalmology, Rockville, Maryland.
Marcelo, K., et al. "The Ca2+/Calmodulin/CaMKK2 Axis: Nature's Metabolic CaMshaft." Trends in Endocrinology & Metabolism, Oct. 2016, 706-718, 27(10), Elsevier Inc., Amsterdam.
Racioppi, L., et al. "Calcium/Calmodulin-dependent Protein Kinase Kinase 2 Regulates Macrophage-mediated Inflammatory Responses." J. Bio. Chem., Mar. 2012, 11579-11591, 287(14), The American Society for Biochemistry and Molecular Biology, Inc., Rockville, Maryland.
Tokumitsu, H., et al. "STO-609, a Specific Inhibitor of the Ca2/Calmodulin-dependent Protein Kinase Kinase." J. Bio. Chem., May 2002, 15813-15818, 277(18), 3, The American Society for Biochemistry and Molecular Biology, Inc., Rockville, Maryland.
Williams, J., et al. "CaMKK2 Signaling in Metabolism and Skeletal Disease: a New Axis with Therapeutic Potential." Curr Osteoporos Rep, Aug. 2019, 169-177, 17, Springer Science+Business Media, LLC, part of Springer Nature, Berlin.
Extended European Search Report dated May 9, 2022 for associated European Patent Application No. 19852526.3 (18 pages).
Database PubChem [Online] Jul. 26, 2002, CA: "Benzimidazo", XP055900419, Database accession Nos. 440322-81-6, 440322-80-5, 440322-79-2, 440322-76-9, 440322-75-8, 440322-7 4-7, 440322-73-6, 440322-72-5, 440322-71-4, 440322-70-3, 440322-69-0, 440322-68-9, 440322-67-8, 440322-66-7, 440322-65-6, 440322-64-5 440322-63-4 440322-62-3 440322-51-0 440322-50-9 440322-49-6440322-48-5, 440322-4 7-4, 440322-46-3, 440322-45-2, 440322-44-1, 440322-43-0, 440322-42-9, 440322-41-8, 440322-40-7, and 440322-39-4 (16 pages).
Database PubChem [Online] Aug. 5, 2002, CA: "Benzimidazo", XP055900418, 5,6-Dihydro-N-[2-(IH-indol-3-yl)ethyl]-6-thioxobenzimidazo[1,2-c]quinazoline-3-carboxamide, Database accession No. 442532-00-5 (1 page.).
Database PubChem [Online] Aug. 9, 2002, CA: "Benzimidazo", XP055900415, Database accession Nos. 443348-42-3, 443348-29-6, and 443348-25-5 (2 pages).
Database PubChem [Online] Aug. 12, 2002, CA: "Benzimidazo", XP055900414, Database accession No. 443671-25-8, 443671-23-6, 443671-21-4, and 443671-07-6 (2 pages).
Database PubChem [Online] Jun. 3, 2004, Ca: "Benzimidazo", XP055900411, Database accession No. 688792-60-1, 688792-59-8, 688792-58-7, 688792-57-6 688792-56-5 688792-55-4 688792-54-3 688792-53-2 688792-52-0, 688792-51-0, 688792-50-9, 688792-49-6, and 688792-44-1 (7 pages).
Database PubChem [Online] Jul. 28, 2006, Ca: "Benzimidazo", XP055900410, Database accession No. 896707-09-08 and 896689-06-8 (1 page).
Database PubChem [Online] Feb. 22, 2008, Ca: "Answer 2", XP055900407, Database accession No. 1005152-37-3 (1 page).
Mai, Shaoyu, et al. "Diversity-oriented synthesis of imidazo[2,1-a]isoquinolines", Chemical Communications, vol. 54, No. 73, XP055900320, pp. 10240-10243 (Jul. 19, 2018).
Database 91522194 [Online] Mar. 17, 2015, "6-Sulfanylidene-5H-benzimidazolo[1,2-c]quinazoline-3-carboxamide | C15H10N4OS", XP055689234, Database accession No. Pubchem Compound (8 pages).
Ivachtchenko, A.V., et al. "Synthesis of substituted 4-oxo-2-thioxo-1,2,3,4-tetrahydroquinazolines and 4-oxo-3,4-dihydroquinazoline-2-thioles". Journal of Combinatorial Chemistry, American Chemical Society, Washington, US, vol. 5, XP003013711, pp. 775-788 (Aug. 16, 2003).
Examination Report issued in related case Australian Application No. 2019326448 dated Jun. 6, 2024.
Office Action dated Jan. 3, 2024 for associated Chinese patent application No. 201980054524X.
Office Action dated Jan. 9, 2024 for associated Japanese patent application JP 2021 509910.
Office Action dated Jan. 17, 2024 for associated Mexican Patent Application No. MX/a/2021/002028.
Office Action (Rejection Decision) dated Feb. 15, 2024 issued by the Taiwanese Patent Office for associated Taiwanese Patent Application 108129703.

\* cited by examiner

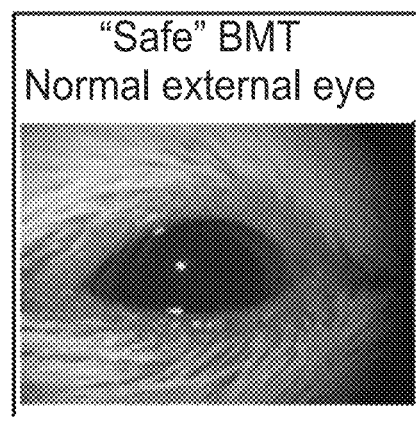
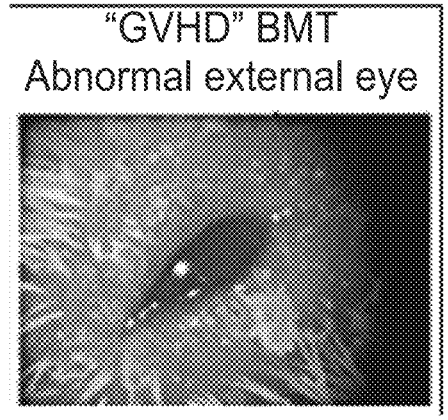
FIG. 7A  FIG. 7B
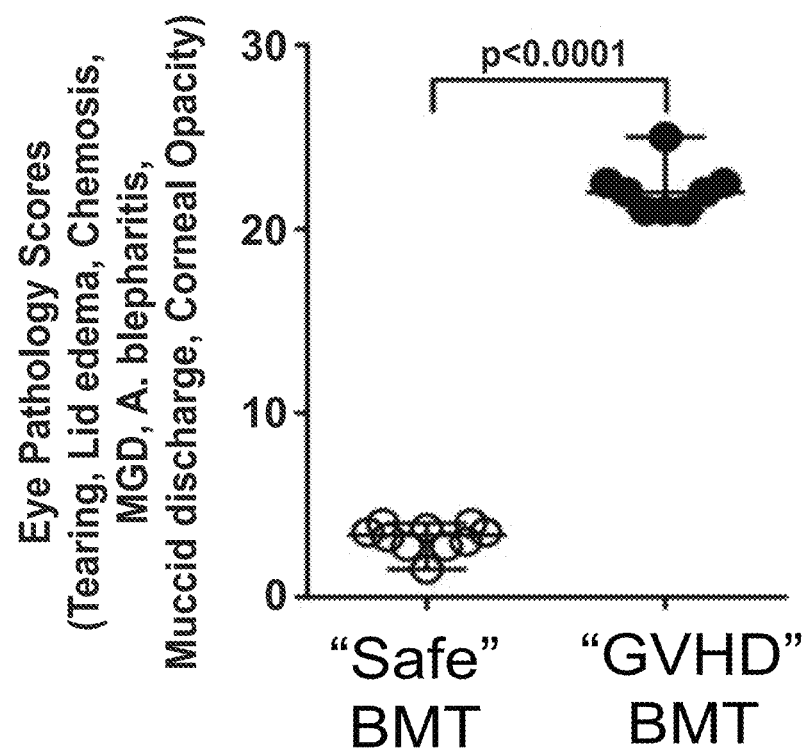
FIG. 8

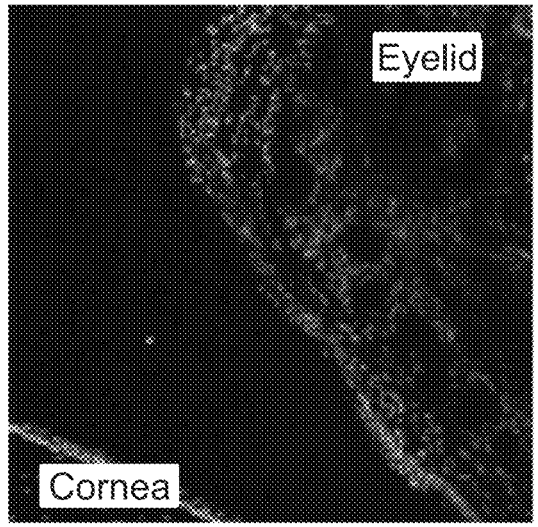
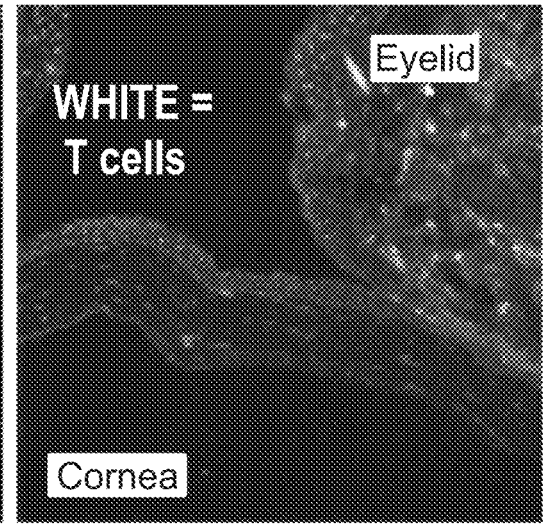
FIG. 10A  FIG. 10B
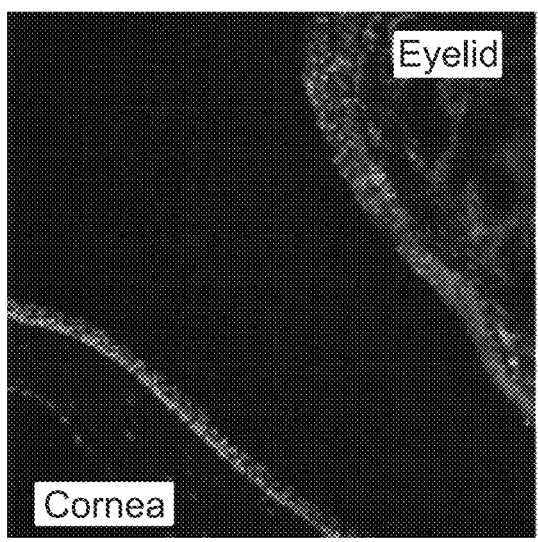
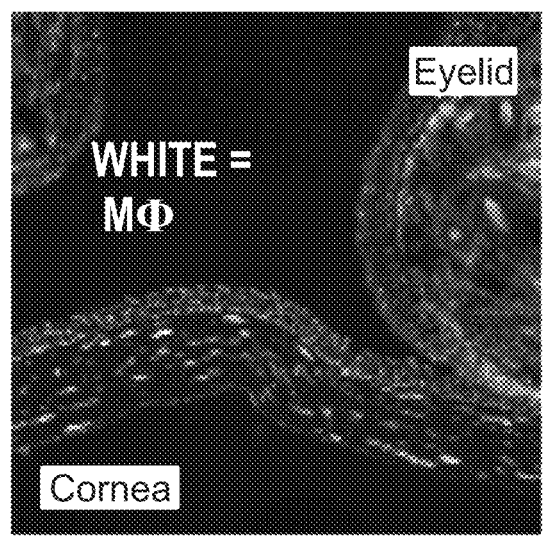
FIG. 10C  FIG. 10D

FIG. 11A                    FIG. 11B

METHODS AND COMPOSITIONS FOR DRUGS TO TREAT OPHTHALMIC DISEASES

CROSS REFERENCE TO RELATED APPLICATIONS

This application is § 371 U.S. National Stage of International Application PCT/US19/47309, filed Aug. 20, 2019, which claims the benefit of U.S. Provisional Application 62/719,938 filed Aug. 20, 2018, Cousins et al., the contents of which are hereby incorporated by reference in their entireties.

STATEMENT REGARDING FEDERALLY SPONSORED RESEARCH OR DEVELOPMENT

This invention was made with government support under Grant Number EY029185-01 awarded by the National Institutes of Health. The government has certain rights in the invention.

1. FIELD

The presently disclosed subject matter relates to compositions and methods for the treatment of ophthalmic diseases mediated by activation of calcium/calmodulin-dependent kinase kinase 2 (CaMKK2), an intermediate kinase that regulates cellular effector functions in a number of cell types, especially immune cells. The primary focus of the presently disclosed subject matter relates to inflammatory diseases of the eye, ocular adnexae, and external tissues (eyelids, orbit). These diseases include anterior segment (or "front of the eye") inflammatory diseases as well as posterior segment (or "back of the eye") diseases in which activation of CaMKK2 in immune cells initiates, mediates, or modulates disease activity; and in which inhibition of CaMKK2 in target immune cells might represent a potential therapeutic or disease-modifying strategy. These include three primary classes of diseases in which CaMKK2 has been shown or is likely to play a role: 1) ocular surface inflammatory diseases (OSIDs), including but not limited to ocular graft versus host disease, ocular cicatricial pemphigoid, vernal keratoconjunctivitis, allergic eye disease, meibomian gland dysfunction, aqueous tear deficiency (common dry eye disease), corneal scarring, and conjunctival scarring and fibrosis; 2) uveitis and other inflammatory diseases of the eye, including but not limited to keratitis, scleritis, iritis, iridocyclitis, intermediate uveitis, pars planitis, posterior uveitis, choroiditis, chorioretinitis, retinitis, or panuveitis of noninfectious, infectious, or idiopathic etiologies; and 3) "back of the eye" retinal diseases, which include but are not limited to dry age-related macular degeneration, neovascular age-related macular degeneration, diabetic retinopathy, retinal vascular diseases (e.g. retinal vein occlusion, retinal artery occlusion), and retinal degenerations and dystrophies.

2. BACKGROUND

2.1. Introduction

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Calcium/calmodulin-dependent protein kinase kinase 2 (CaMKK2) is an intracellular intermediate kinase that is ubiquitously expressed in many cell types. However, the activity of CaMKK2 is particularly increased within certain "activated" cells, including cells of the immune system, especially activated T lymphocytes and infiltrating macrophages (1-5). CaMKK2 appears to be an amplifier of effector functions for "activated" cells more than a maintainer of homeostasis. Accordingly, in experimental studies, mice null for CaMKK2 demonstrate no major phenotype, including no evidence of immunodeficiency. CaMKK2 is one of the most important calcium responsive kinases, and its activity is regulated by cytoplasmic calcium and calmodulin levels. Once active, CaMKK2 phosphorylates several substrates. In addition to auto-phosphorylating and activating other CaMKK2 molecules, CaMKK2 directly phosphorylates calcium/calmodulin-dependent protein kinase I (CaMKI), calcium/calmodulin-dependent protein kinase IV (CaMKIV), and adenosine monophosphate-activated protein kinase (AMPK) (FIGS. 1 and 2). Phosphorylation of these substrates amplifies multiple downstream signaling cascades, modulating multiple cellular effector functions.

CaMKK2 Activity in T Cells:

Via phosphorylation of its substrates CaMKI, CamKIV, and AMPK, CaMKK2 regulates a number of specific effector functions in T cells (FIG. 1). In activated T lymphocytes, calcium is the major secondary messenger system, irrespective of activation via T cell receptor or amplification by co-stimulatory signals and/or IL-2 (6), resulting in activation of calmodulin and CaMKK2. In activated T cells, downstream activation of AMPK regulates cellular bioenergetics, proliferation, and cytokine production (1, 5). CaMKI regulates T cell migration and adherence (7). CaMKIV is important in T cell cytokine effector responses. CaMKK2 also amplifies activation of PTK2B (protein tyrosine kinase beta), which mediates the p38 MAPK pathway, crucial for production of many effector cytokines (3). Thus, not surprisingly, knockout of CaMKK2 diminishes T cell-mediated inflammation in a number of inflammatory diseases, such as experimental graft versus host disease (GVHD) (2, 8-11).

CaMKK2 Activity in Macrophages:

Via phosphorylation of its substrates CaMKI, CamKIV, and AMPK, CaMKK2 is also a major regulator of macrophage function (FIG. 2). For example, activation of AMPK turns on a whole host of gene transcription important for reparative function in nonclassical macrophages, and specific inhibition of CaMKK2 inhibits transition of monocyte-to-nonclassical macrophages via prevention of AMPK activation (12). As in T cells, CaMKK2 also amplifies activation of PTK2B (protein tyrosine kinase beta), which mediates the p38 MAPK pathway, crucial also for production of many macrophage-derived effector cytokines (3). Thus, CaMKK2 inhibition decreases production of pro-inflammatory cytokine that have been implicated in tissue injury and destruction. Increased activity of CaMKK2 is observed in macrophages previously exposed to activating stimuli (e.g. LPS) (lipopolysaccharide) (4). Knockout of CaMKK2 impairs the ability of macrophages to adhere and extend membrane processes, resulting in reduced macrophage accumulation and diminished cytokine release in response to such activating stimuli (4).

Rationale as Therapeutic Target for Ophthalmic Diseases:

OSIDs and uveitic diseases are well established as disorders with significant ocular morbidity and vision loss, and inflammatory cells (especially macrophages) are also known to contribute to the severity and visual morbidity of posterior segment diseases (13-17). All of these conditions can include both diseases in which immune cells, especially T cells and macrophages, are the primary mediators of disease (i.e. these cells infiltrate ocular tissues and trigger local injury as a primary disease process) and diseases in which immune cells are secondary pathologic mediators in response to a primary ocular disease process. In both T cells and macrophages, CaMKK2 functions as an amplification circuit; knockout diminishes inflammation but does not induce immunosuppression (4). Thus, CaMKK2 represents an attractive therapeutic target in ocular inflammatory diseases when taken together with the established role of CaMKK2 in T cell and macrophage function. Importantly, preclinical data from experimental mouse models of ocular inflammatory disease demonstrate that targeted inhibition of CaMKK2 ameliorates disease severity, with reduced infiltration of T cells and macrophages (See Examples 4 and 5 of this application). Data from these and other models of ocular disease provide compelling rationale and proof-of-concept for the development and potential efficacy of small molecule inhibitors of CaMKK2 for the treatment of ophthalmic diseases, especially those mediated primarily or secondarily by inflammatory or immune cells.

3. SUMMARY OF THE DISCLOSURE

The presently disclosed subject matter relates to compositions and methods for novel small molecule inhibitors of calcium/calmodulin-dependent protein kinase kinase 2 (CaMKK2), an intermediate kinase that has increased activity within cells of the immune system, including activated T cells and macrophages. Novel small molecules have been designed with high specificity and efficacy for inhibition of CaMKK2, and these molecules retain hydrophilicity and high aqueous solubility. The biophysical properties of these small molecule inhibitors of CaMKK2 (SMICs) allow them to be readily formulated in aqueous solution or suspension. Thus, these SMICs are ideally suited for treatment of ophthalmic diseases via topical or subconjunctival routes of ocular administration.

Another aspect of the present disclosure provides all that is disclosed and illustrated herein.

4. BRIEF DESCRIPTION OF THE FIGURES

The previous summary and the following detailed descriptions are to be read in view of the drawings, which illustrate some (but not all) embodiments of the presently disclosed subject matter.

FIG. 7A is a slit lamp biomicroscopic photograph of the external eye of a mouse after receiving a "safe" blood marrow transplant (i.e. no concurrent T cell adoptive transfer).

FIG. 7B is a slit lamp biomicroscopic photograph of the external eye of a mouse, depicting ocular graft versus host disease (OGVHD) following an allogenic blood marrow transplant with concurrent adoptive transfer of splenic T cells.

FIG. 8 is a scatter plot of OGVHD eye pathology scores of "GVHD" BMT mice (with concurrent adoptive transfer of splenic T cells), as compared to minimal OGVHD severity in "safe" BMT mice.

FIG. 10A-10D are images showing histopathologic evidence of T cell (A and B) and macrophage (C and D) infiltration into the corneal stroma, bulbar, and tarsal conjunctiva.

FIG. 11A is a slit lamp biomicroscopic photograph of the eye of a control-treated mouse with OGVHD.

FIG. 11B is a slit lamp biomicroscopic photograph of a STO-609 treated mouse, with minimal signs of OGVHD following treatment.

Figure 12:
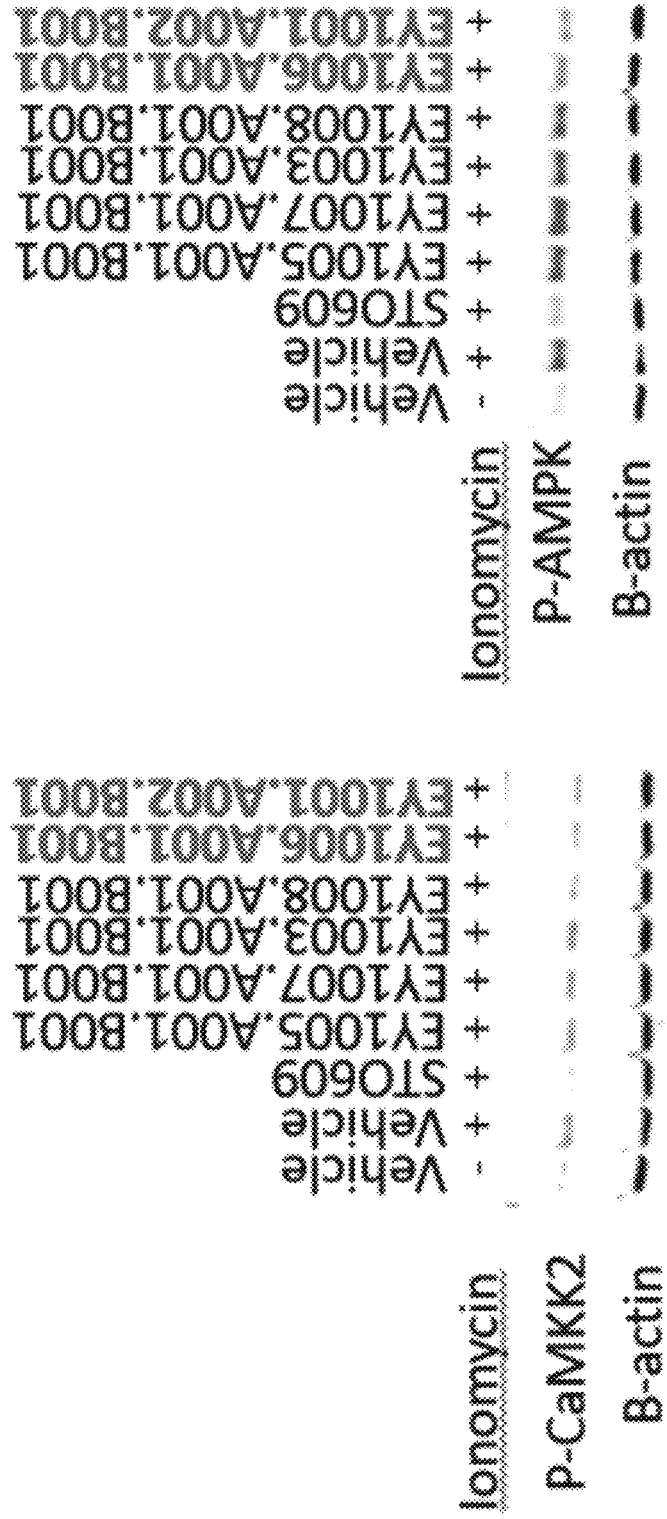

FIG. 12: Candidate SMICs demonstrate similar potency to STO-609 in vitro. HEK-293 cells were treated with STO-609, candidate SMICs, or vehicle control prior to stimulation with 1 mM ionomycin, a known activator of CaMKK2. Cell lysates were then probed with phospho-specific antibodies to CaMKK2 and AMPK. B-actin was used as a loading control. Graphs show quantification of densitometry with corrections for loading variation.

Figure 13:
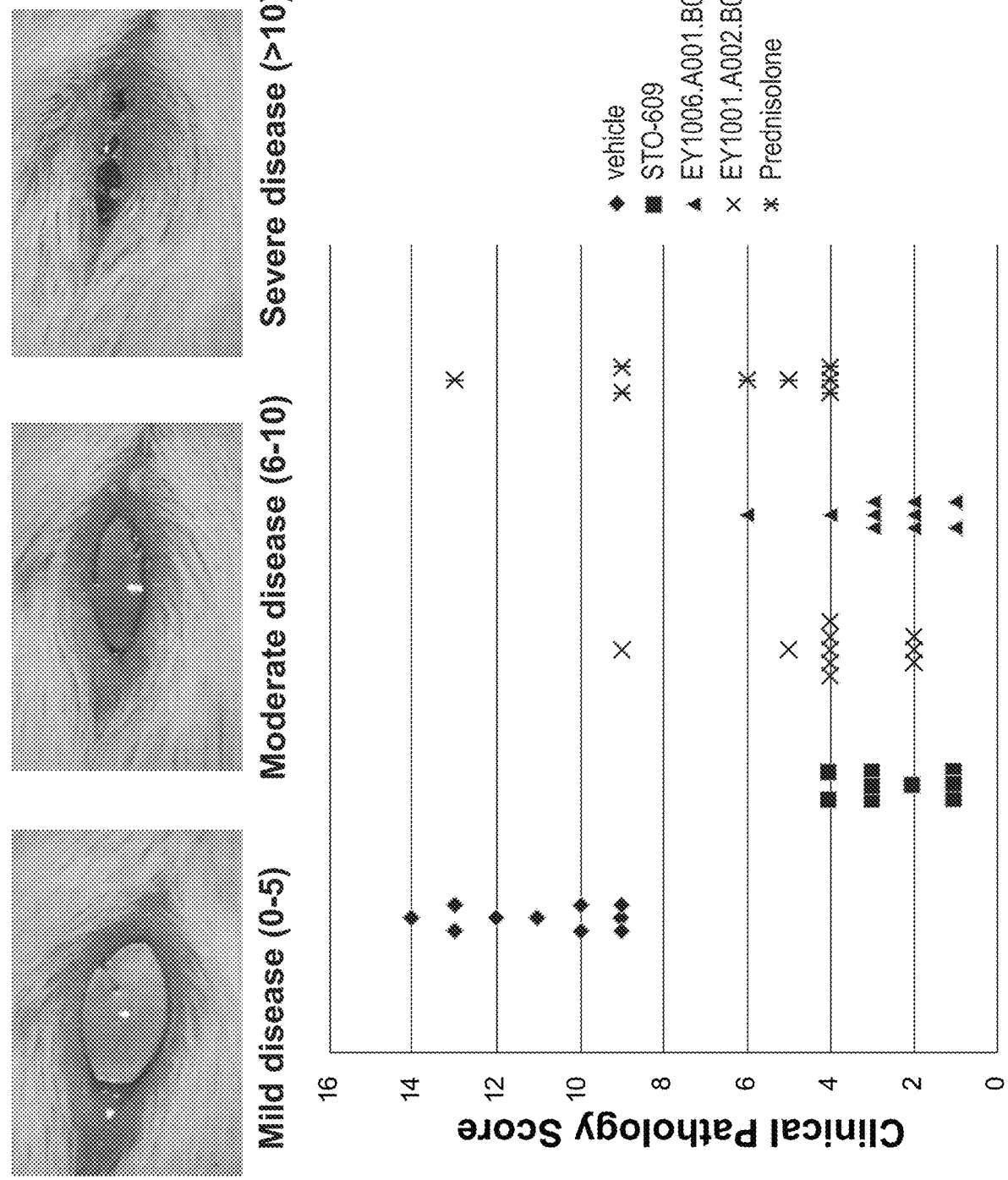

FIG. 13: Mice underwent local ocular administration of the tool compound inhibitor of CaMKK2, STO-609, lead SMIC compounds EY1006.A001.B001 and EY1001.A002.B001, prednisolone starting at day 14 post-BMT and continuing for two weeks. Both lead SMICs EY1006.A001.B001 and EY1001.A002.B001 reduced severity of clinical OGVHD findings with efficacy similar to STO-609. By contrast, vehicle control-treated eyes had lid margin swelling and scarring with lash and periocular fur loss, eyelid crusting, chemosis, abnormal tear film, and keratopathy. STO-609 and lead SMICs were superior to vehicle and prednisolone, in preventing signs of OGVHD (p<0.05 for STO-609, EY1006.A001.B001, EY1001.A002.B001 vs vehicle or prednisolone). Mild disease (score 0-5); moderate disease (score 6-10); severe disease (score >10).

5. DETAILED DESCRIPTION OF THE DISCLOSURE

5.1. Definitions

While the following terms are believed to be well understood by one of ordinary skill in the art, the following definitions are set forth to facilitate explanation of the presently disclosed subject matter.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a cell" can include a plurality of such cells, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

The presently disclosed subject matter is based on the discovery of calcium/calmodulin kinase kinase 2 (CaMKK2) as a target for activated T cells and macrophages. CaMKK2 is an enzyme encoded by the CAMKK2 gene (18) and was first proposed to be a key mediator of central nervous system appetite control in 2008, as it was shown to be present in centers of the brain controlling satiety (19). More recently, CaMKK2 has been shown to be an important regulatory kinase in macrophages and T cells (FIGS. 1 and 2), and consequently has important effects on macrophage-mediated and T cell-mediated biology in various diseases, including certain cancers, appetite control and satiety, and various immune-mediated and inflammatory diseases at multiple tissues sites within the body (1-5, 19-21). The term "disease" as used herein includes various diseases, disorders, symptoms, conditions, and/or indications.

Figure 1:
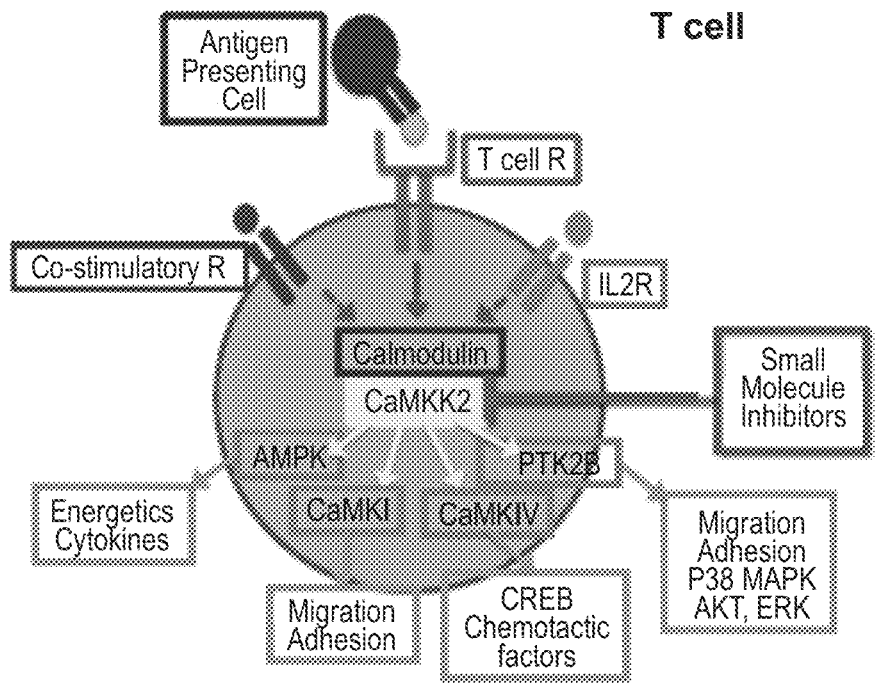
FIG. 1 is a schematic illustrating CaMKK2 regulation of T cell effector responses, and how CaMKK2 amplification of multiple downstream pathways mediates many proinflammatory effector mechanisms.

CaMKK2 belongs to the Serine/Threonine protein kinase family, and to the $Ca^{+2}$/calmodulin-dependent protein kinase subfamily (18). Further, CaMKK2 is regulated by cytoplasmic calmodulin levels and inflammatory stimuli. In active T cells, calcium is the major secondary messenger system, irrespective of activation via T cell receptor or amplification by co-stimulatory signals and/or IL-2 (6). In addition to autophosphorylating and activating other CaMKK2 molecules, CaMKK2 phosphorylates calcium/calmodulin-dependent kinase I and IV (CaMKI and CaMKIV) and adenosine monophosphate-activated protein kinase (AMPK), which regulate numerous T cell functions (1, 2, 5, 6, 8, 10), as shown in FIG. 1. Particularly, CaMKI regulates T cell migration and adherence (6), and CaMKIV is important in T cell cytokine effector responses (2, 6, 8, 10). Further, AMPK regulates T cell bioenergetics, proliferation, and cytokine production (1, 5, 6). Activation of these kinases and downstream signaling pathways promote T cell activation and subsequent inflammation. CaMKK2 also amplifies activation of protein tyrosine kinase beta (PTK2B) (3, 4), which mediates many proinflammatory and fibrogenic effector systems. Importantly, CaMKK2 functions as an amplification circuit such that knockout diminishes inflammation but does not induce immunosuppression (3, 4).

Figure 2:
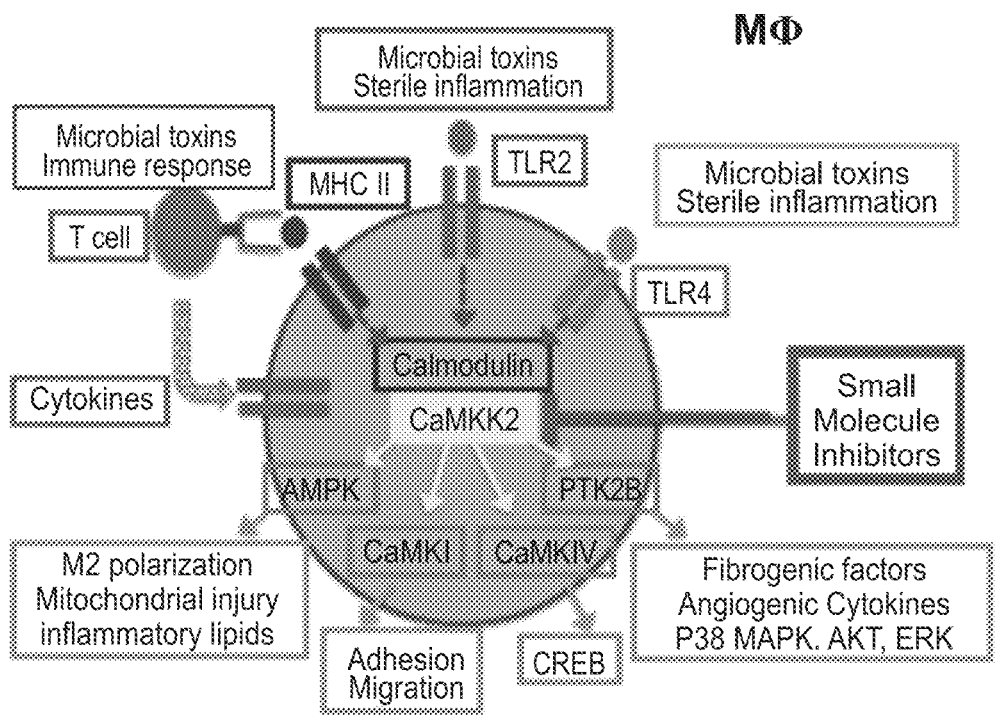
FIG. 2 is a schematic illustrating CaMKK2 regulation of macrophage effector responses, and how CaMKK2 amplification of multiple downstream pathways mediate both proinflammatory and profibrotic effector mechanisms.

CaMKK2 is also a major regulator of macrophage function, as shown in FIG. 2. Activation of AMPK by CaMKK2 turns on a whole host of gene transcription important for reparative function in nonclassical macrophages (3, 4, 12), and specific inhibition of CaMKK2 inhibits transition of monocyte-to-nonclassical macrophages via prevention of AMPK activation (12). CaMKK2 also amplifies activation of PTK2B (protein tyrosine kinase beta), which mediates the p38 MAPK pathway, crucial also for production of many macrophage-derived effector cytokines (3, 4). Thus, CaMKK2 inhibition decreases production of pro-inflammatory cytokine that have been implicated in tissue injury and destruction. Increased activity has been observed in macrophages previously exposed to activating stimuli (3, 4). Further, knockout of CaMKK2 impairs the ability of macrophages to adhere and extend membrane processes, resulting in reduced macrophage accumulation and diminished cytokine release in response to certain toxins (e.g., LPS) (4).

Taken together, these findings provide a strong rationale for the inhibition of CaMKK2 as a therapeutic strategy in T cell and macrophage-mediated diseases. Significantly, inhibition of CaMKK2 allows for dual targeting of T cells and macrophages in any ophthalmic disease in which both cell types play a role. These include: 1) ocular surface inflammatory diseases (OSIDs), including but not limited to ocular graft versus host disease, ocular cicatricial pemphigoid, vernal keratoconjunctivitis, allergic eye disease, meibomian gland dysfunction, aqueous tear deficiency (common dry eye disease), corneal scarring, and conjunctival scarring and fibrosis; 2) uveitis and other inflammatory diseases of the eye, including but not limited to keratitis, scleritis, iritis, iridocyclitis, intermediate uveitis, pars planitis, posterior uveitis, choroiditis, chorioretinitis, retinitis, or panuveitis of noninfectious, infectious, or idiopathic etiologies; and 3) "back of the eye" retinal diseases, which include but are not limited to dry age-related macular degeneration, neovascular age-related macular degeneration, diabetic retinopathy, retinal vascular diseases (e.g. retinal vein occlusion, retinal artery occlusion), and retinal degenerations and dystrophies.

Figure 3A:
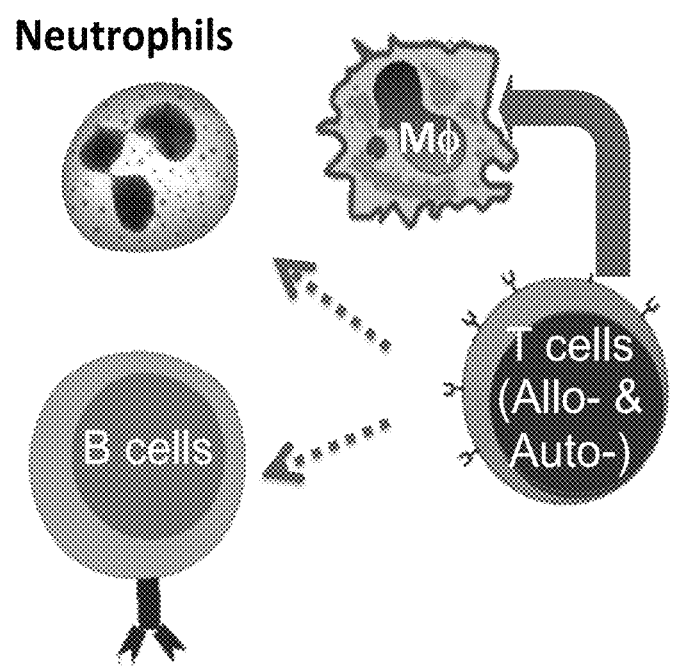
FIG. 3A is a schematic illustrating the pathobiology of ocular graft versus host disease after allogeneic hematopoietic stem cell transplantation (HSCT) (i.e. bone marrow transplant).
Figure 3B:
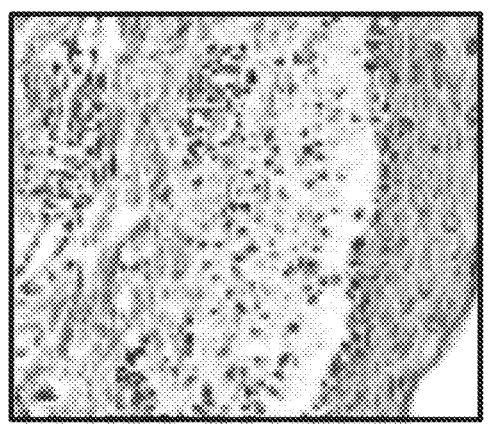
FIG. 3B is a hematoxylin and eosin (H&E) micrograph image depicting histology of immune cell (T cell and macrophage) infiltration of conjunctiva in OGVHD.
Figure 3C:
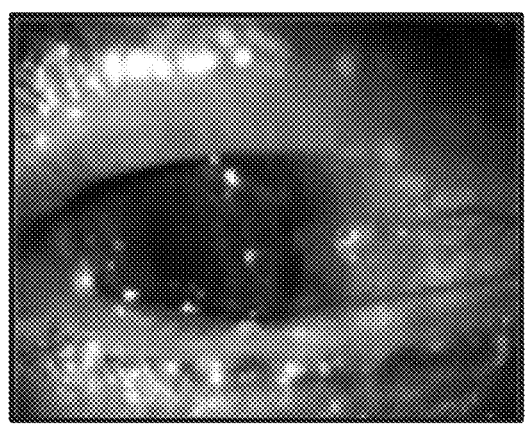
FIG. 3C is a clinical slit-lamp biomicroscopic photograph illustrating a clinical presentation of severe OGVHD.

Among these disorders, ocular graft versus host disease (OGVHD) represents a model ocular inflammatory disease (FIG. 3) to characterize the therapeutic potential of novel small molecule inhibitors of CaMKK2 (SMICs), since clinical and pathologic findings of the disease can be characterized in a well-defined patient population (i.e. those patients undergoing bone marrow transplant) (13, 15, 22); both T cells and macrophages are known to play a pathogenic role in OGVHD (14, 23); and the disease can treated by ocular drug administration (23). OGVHD occurs in over 60% of patients undergoing allogeneic hematopoietic stem cell transplant (HSCT) (i.e. bone marrow transplant) (13, 15). In OGVHD, donor T cells encounter recipient transplantation antigens within ocular tissue, leading to T cell activation and cytokine production (FIG. 3A) (14, 23). This triggers recruitment and infiltration of donor macrophages, additional "autoimmune" T cells, with secondary contribution of neutrophils and B cells (14, 23) (FIG. 3B). These infiltrating inflammatory cells serve as "effectors" of tissue damage. Clinically, OGVHD manifests as findings of aqueous tear deficiency, Meibomian gland dysfunction, keratopathy, and in severe cases, conjunctival scarring, lid margin scarring, and corneal ulceration (FIG. 3C) (13, 24, 25). Since OGVHD shares clinical and pathologic overlap with more common OSIDs (i.e. common dry eye, Meibomian gland dysfunction, others), and with other ocular inflammatory diseases (i.e. various forms of uveitis) (26-29), experimental preclinical models of OGVHD represent ideal systems to study the therapeutic potential of drugs that target and inhibit CaMKK2.

The small molecule STO-609 is a well characterized and specific inhibitor of CaMKK2 (30). Though the biophysical properties of STO-609 have limited its potential as a therapeutic, the molecular interaction of STO-609 with CaMKK2 provides important insights into specific characteristics that enable inhibition of CaMKK2 activity. The planar, rigid STO-609 molecule fits into a narrow pocket within the kinase domain, competing with and preventing ATP binding. The binding pocket interactions between STO-609 and CaMKK2 are predominantly hydrophobic in nature (i.e., especially at the CaMMK2 peptide interacting residues Ile171, Val179, Ala192, Val249, Phe267, Gly273, Pro274, and Leu319). In addition to the hydrophobic interactions, two key hydrogen bonding interactions help accommodate STO-609 binding within the active site—(i) the interaction between the STO-609 amide oxygen and Val270; and (ii) the interaction between the carboxylic acid of bound STO-609 and Asp330. Further, an active site molecule of water forms a hydrogen bond bridge between the carboxylic acid of STO-609 and Glu236. Collectively, these molecular interactions enable STO-609 inhibitory capacity of CaMKK2. STO-609 has $K_i$ for CaMKK2<30 nM and IC50<40 nM in HeLa cells and IC50 of about 100 nM in macrophages and T cells (31). Further, STO-609 displays 6-fold less activity for CaMKK1 and >80-fold selectivity for CaMKK2 over CaMKI, CaMKII, CaMKIV, MLCK, PKC, PKA, p42, MAPK, VEGFR1, and PDGFR (30).

However, despite such promising activity, STO-609 suffers from several limitations that render it useful only as a tool compound. For example, the current synthetic route universally employed to synthesize STO-609 at scales of about 100 mg or more yields a pair of isomeric bromides that comprise as much as 40-50% of the mixture, as shown below.

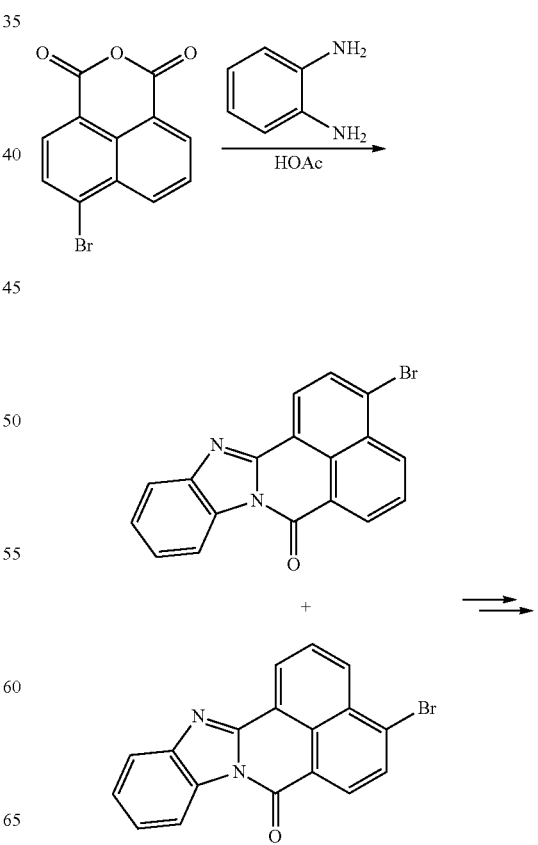

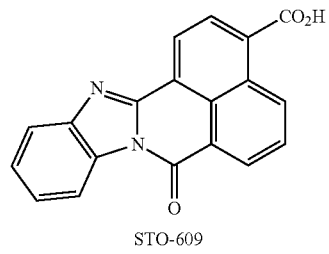

STO-609

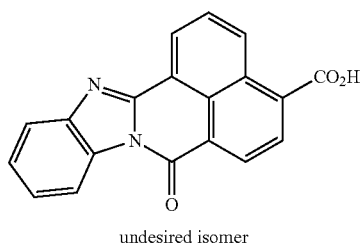

undesired isomer

In addition, STO-609 exhibits poor solubility (i.e., the maximum concentration of STO-609 in DMSO is 10 mM with sonication) such that in vivo and in vitro work with the compound leads to precipitation. STO-609 also exhibits poor oral bioavailability, which limits its development as a therapeutic and restricts its use as a tool compound for laboratory studies. Further, various off-target effects have been suspected, including activation of aryl hydrocarbon receptors (32). With knowledge of the biochemical structure of STO-609, the inventors were able to design formulations for local ocular (i.e., periocular and topical) application of STO-609. Additionally, with knowledge of STO-609 orientation in the CaMKK2 binding pocket, the inventors were able to determine which regions of STO-609 are best suited for structural alteration and addition of groups to the molecular framework that could enhance aqueous solubility.

(I)

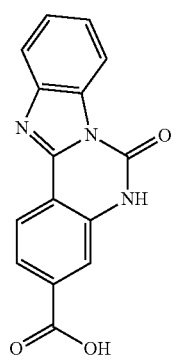

(II)

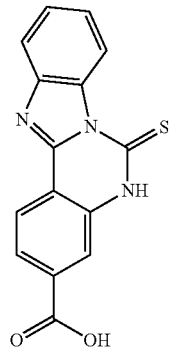

The presently disclosed subject matter further comprises pharmaceutically acceptable salts, solvates, hydrates, prodrugs, and/or derivatives of the compounds of Formulas (I) and (II). The term "pharmaceutically acceptable" as used herein refers to generally recognized for use in animals, such as (but not limited to) humans, and that are not biologically or otherwise undesirable in a subject.

The benzimidazole urea scaffold of the compound of Formula (I) maintains a flat, rigid aromatic structure, similar to STO-609, as shown below.

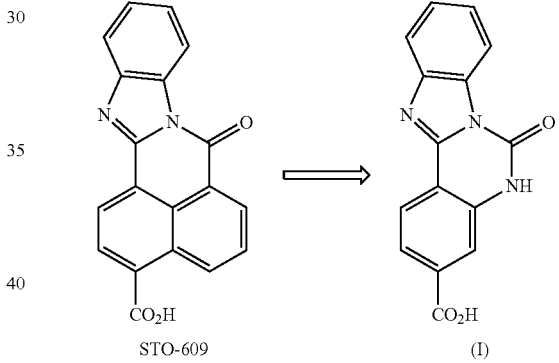

STO-609        (I)

Thus, the shallow and narrow binding pocket of CaMKK2 remains accessible to the disclosed series of inhibitors. Further, CaMKK2 active site docking simulations using AutoDock® (available from Scripps Research Institute, La Jolla, Calif.) with the compound of Formula (I) have confirmed that stabilizing hydrogen bond interactions with Val270, Asp330, and Glu236 are maintained with the urea oxygen and carboxylate groups, respectively. Structurally, the major improvement with the transition to the benzimidazole urea scaffold compound of Formula (I) is the loss of an aromatic ring. As a result, the c log D decreases by an order of magnitude (c log $D(STO-609)_{7.4}$=−0.75, c log $D(I)_{7.4}$=−1.75), enhancing solubility of the essential scaffold. However, modifications to core structure will allows considerable versatility for creating novel analog compounds with high aqueous solubility for topical administration. While it is possible that active site stabilization of the inhibitor through interactions with Phe267 and Val179 will be lost, compensation for the loss can be realized through urea NH hydrogen bonding to the C=O of backbone residue E269.

In addition, unlike the synthesis of STO-609, the compositions of Formulas (I) and (II) (and all current and proposed benzimidazole urea series compounds disclosed herein) produce a single compound. As a result, the production of non-binding isomers does not occur, enhancing both efficiency and fidelity of expected synthetic products even for large-scale synthesis.

The presently disclosed subject matter further includes synthetically accessible structural analogs of Formulas (I) and (II), such as (but not limited to) the compounds of subseries Formulas (III) through (V), and to pharmaceutically acceptable salts, solvates, hydrates, prodrugs, or derivatives thereof, wherein R comprises an alkyl, heteroalkyl, cycloalkyl, heterocycloalkyl, aryl, or heteroaryl group.

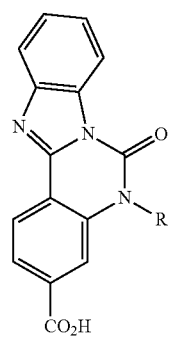

(III)

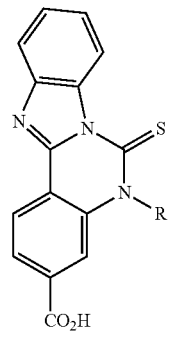

(IV)

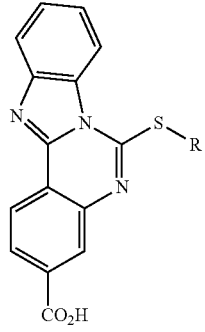

(V)

The term "alkyl," by itself or as part of another substituent, means, unless otherwise stated, a straight (i.e., unbranched) or branched chain, or combination thereof, which may be fully saturated, mono- or polyunsaturated (i.e., alkenyl) and can include di- and multivalent radicals (e.g., alkylene), having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups (i.e., alkenyl groups) include, but are not limited to, vinyl, 2-propenyl, 2-isopentenyl, 2-(butadienyl), 2,4-pentadienyl, 3-(1,4-pentadienyl), ethynyl, 1- and 3-propynyl, 3-butynyl, and the higher homologs and isomers. The alkyl group may be substituted or unsubstituted; for example with one or more halogens, e.g., trifluoromethyl.

The term "heteroalkyl," by itself or in combination with another term, means, unless otherwise stated, a stable straight or branched chain, or combinations thereof, consisting of at least one carbon atom and at least one heteroatom. A "heteroatom" includes oxygen (O), nitrogen (N), sulfur (S), phosphorus (P), selenium (Se) and silicon (Si), wherein N and S may optionally be oxidized, and N may optionally be quaternized. A heteroatom(s) may be placed at any chemically acceptable position including an interior position, the position at which the alkyl group is attached to the remainder of the molecule (the proximal end), or at the distal end (e.g., for heteroalkylene groups). Examples include but are not limited to: —C(O)R', —C(O)NR', —NR'R'', —OR', —SR', and/or –$SO_2$R', and —CN. Up to two heteroatoms may be consecutive, such as, for example, $CH_2$—NH—$OCH_3$.

The terms "cycloalkyl" and "heterocycloalkyl" by themselves or in combination with other terms, mean, unless otherwise stated, cyclic versions of "alkyl" and "heteroalkyl," respectively. Examples of cycloalkyl include, but are not limited to, cyclopropyl, cyclobutyl, cyclopentyl, cyclohexyl, and cycloheptyl. Examples of heterocycloalkyl include, but are not limited to, piperidinyl, piperazinyl, morpholinyl, tetrahydrofuranyl, and tetrahydrothienyl. The cycloalkyl or heterocycloalkyl group may be substituted or unsubstituted.

The term "aryl" by itself or in combination with another term, means, unless otherwise stated, a polyunsaturated, aromatic, hydrocarbon group, which can be a single ring or multiple rings (preferably from 1 to 3 rings) that are fused together or linked covalently. A fused ring aryl refers to multiple rings fused together wherein at least one of the fused rings is an aryl ring.

The term "heteroaryl" by itself or in combination with another term, means, unless otherwise stated an aryl group (as defined above) containing one to four heteroatoms (as defined above). Thus, the term "heteroaryl" includes fused ring heteroaryl groups, which are multiple rings (e.g., 5 and/or 6-membered rings) fused together wherein at least one of the fused rings is a heteroaromatic ring. A heteroaryl group can be attached to the remainder of the molecule through a carbon or heteroatom. Non-limiting examples of aryl and heteroaryl groups include phenyl, naphthyl, pyrrolyl, pyrazolyl, imidazolyl, pyrazinyl, oxazolyl, thiazolyl, furyl, thienyl, pyridyl, pyrimidyl, purinyl, benzothiazolyl, benzimidazolyl, indolyl, isoquinolyl, quinoxalinyl, 5-quinoxalinyl, and quinolyl. The aryl or heteroaryl group may be substituted or unsubstituted, for example with a halogen. The aryl or heteroaryl group may be mono-, di- or tri-substituted.

Further, the presently disclosed subject matter includes benzimidazole cyclic (thio)urea subseries compounds, such as (but not limited to) the compounds of Formulas (VI) and (VII), and to pharmaceutically acceptable salts, solvates, hydrates, prodrugs, or derivatives thereof, wherein X is oxygen (O) or sulfur (S), and n is 1 or 2.

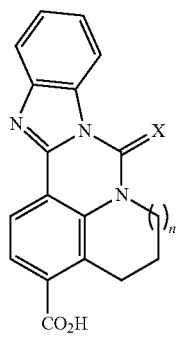

(VI)

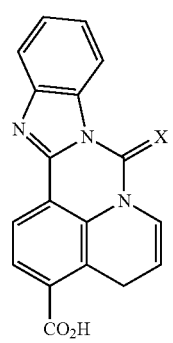

(VII)

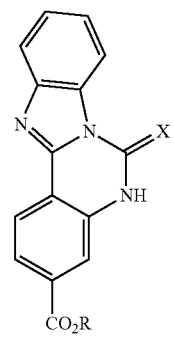

(VIII)

The presently disclosed subject matter further includes benzimidazole thio(urea) carboxamide subseries compounds. The term "carboxamide" as used herein refers to a moiety comprising a carbon, nitrogen, and oxygen atom bonded in the configuration shown as Formula A. Specifically, the carbon atom is bonded to a carbon atom in a radical to which the carboxamide moiety is bonded. Further, the nitrogen atom is bonded to the carbonyl carbon and is also bonded to two other atoms, at least one of which is selected from a hydrogen atom or a carbon atom of another radical to which the carboxamide moiety is bonded.

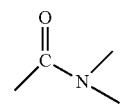

(A)

The presently disclosed subject matter also includes benzimidazole thio(urea) ester prodrug subseries compounds. The term "ester" as used herein refers to any chemical compound derived by the reaction of an oxoacid (an organic acid that contains oxygen) with a hydroxyl compound, such as an alcohol. Esters are usually derived from an organic acid in which at least one hydroxyl (—OH) group is replaced by an —O-alkyl (alkoxy) group. Most commonly, esters are formed by condensing a carboxylic acid with an alcohol. The term "prodrug" as used herein refers to a compound that exhibits no significant pharmacological activity unless it is converted to a pharmacologically active parent compound. Typically, pharmaceutically useful prodrugs are compounds that upon administration to an individual are converted in vivo to the corresponding pharmacologically active parent compound. However, suitable prodrugs can also be converted to the pharmacologically active parent drug in vitro in the presence of an exogenously provided converting activity, such as (but not limited to) a converting enzyme.

For example, suitable benzimidazole thio(urea) ester prodrug compounds can include those of Formula (VIII), and to pharmaceutically acceptable salts, solvates, hydrates, or derivatives thereof, wherein X is O or S, and R is an ester prodrug.

For example, suitable benzimidazole thio(urea) carboxamide compounds can include (but are not limited to) compounds of Formulas (IX) through (XI), and to pharmaceutically acceptable salts, solvates, hydrates, prodrugs, or derivatives thereof, wherein X is O or S; R is alkyl, heteroalkyl, cycloalkyl, heterocycloalkyl, aryl, or heteroaryl groups; and $R_1$ and $R_2$ are the same of different alkyl, heteroalkyl, cycloalkyl, heterocycloalkyl, aryl, or heteroaryl groups.

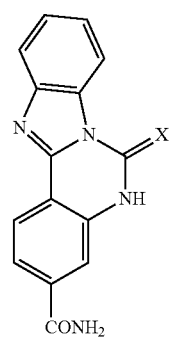 [SMILES: O=C(O)c1ccc2c(c1)[nH]c(=O)n1c3ccccc3nc21]

(IX)

(X)

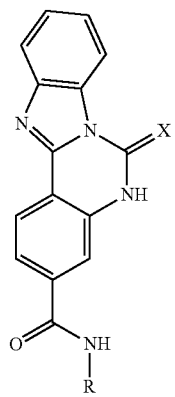

(XI)

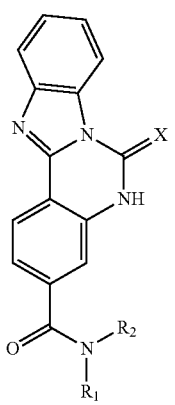

(XII)

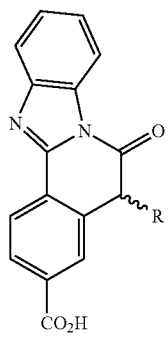

(XIII)

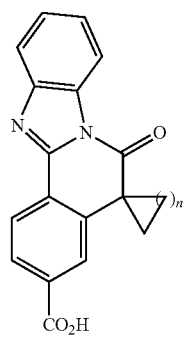

(XIV)

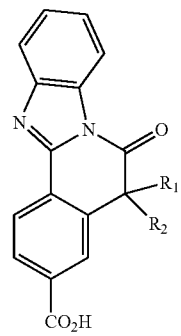

(XV)

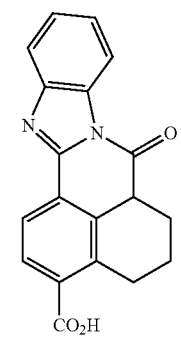

In some embodiments, the presently disclosed subject matter includes benzimidazole aliphatic and alicyclic subseries compounds. The term "aliphatic" as used herein refers to an organic compound characterized by a straight or branched chain structure, or closed ring structure that includes saturated carbon bonds and optionally one or more unconjugated unsaturated bonds, such as a carbon-carbon double bond. The term "alicyclic" as used herein refers to an organic compound that includes a closed ring structure comprising saturated carbon bonds and optionally one or more unconjugated carbon-carbon double bonds.

For example, suitable benzimidazole aliphatic and alicyclic subseries compounds can include the compounds of Formulas (XII) through (XV), and to pharmaceutically acceptable salts, solvates, hydrates, prodrugs, or derivatives thereof, wherein n is 1, 2, or 3; R is alkyl, heteroalkyl, cycloalkyl, heterocycloalkyl, aryl, or heteroaryl groups; and $R_1$ and $R_2$ are the same of different alkyl, heteroalkyl, cycloalkyl, heterocycloalkyl, aryl, or heteroaryl groups.

In some embodiments, the presently disclosed subject matter includes aryl and hetaryl benzimidazole urea compounds, such as the compounds of Formula (XVI), and to pharmaceutically acceptable salts, solvates, hydrates, prodrugs, or derivatives thereof.

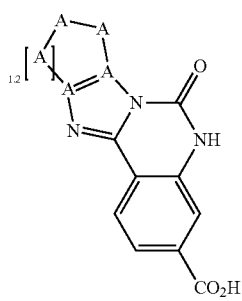

(XVI)

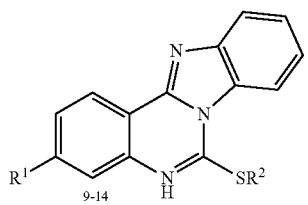

(XIX)

In some embodiments, the presently disclosed subject matter includes benzimidazole (thio)urea subseries compounds that include an sp³ hybridized carbon atom. An sp³ hybridized carbon atom refers to a carbon atom that forms four bonds to four substituents placed in a tetragonal fashion around the carbon atom. Suitable benzimidazole (thio)urea subseries compounds that include an sp³ hybridized carbon atom include (but are not limited to) compounds of Formula (XVII), and to pharmaceutically acceptable salts, solvates, hydrates, prodrugs, or derivatives thereof, wherein X is O or S.

In some embodiments, the compound has the structure:

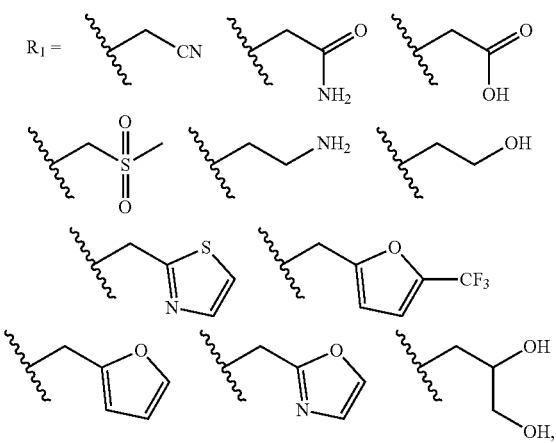

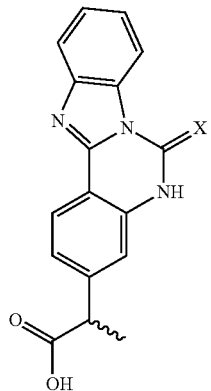

(XVII)

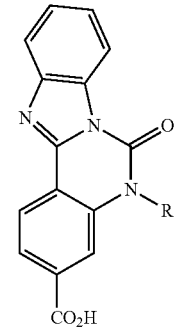

The presently disclosed subject matter further includes synthetically accessible structural analogs of Formulas (I) and (II), such as (but not limited to) the compounds of subseries Formulas (XVIII) and (XIX), and to pharmaceutically acceptable salts, solvates, hydrates, prodrugs, or derivatives thereof, wherein $R_1$ comprises H or $COOCH_3$, and $R_2$ is $CH_2CN$, $CH_2COOC_2H_5$, or $CH_2COPh$.

The compounds above and compounds 1-9 of Table 1 are synthesized using the scheme below:

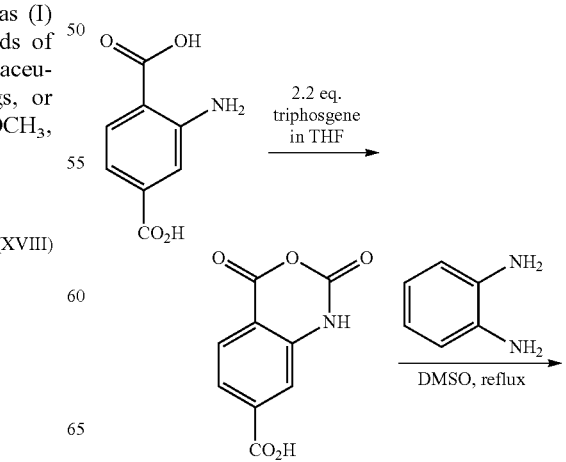

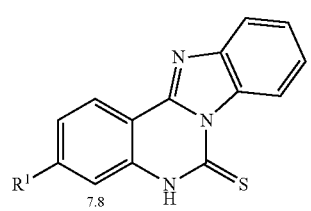

(XVIII)

-continued
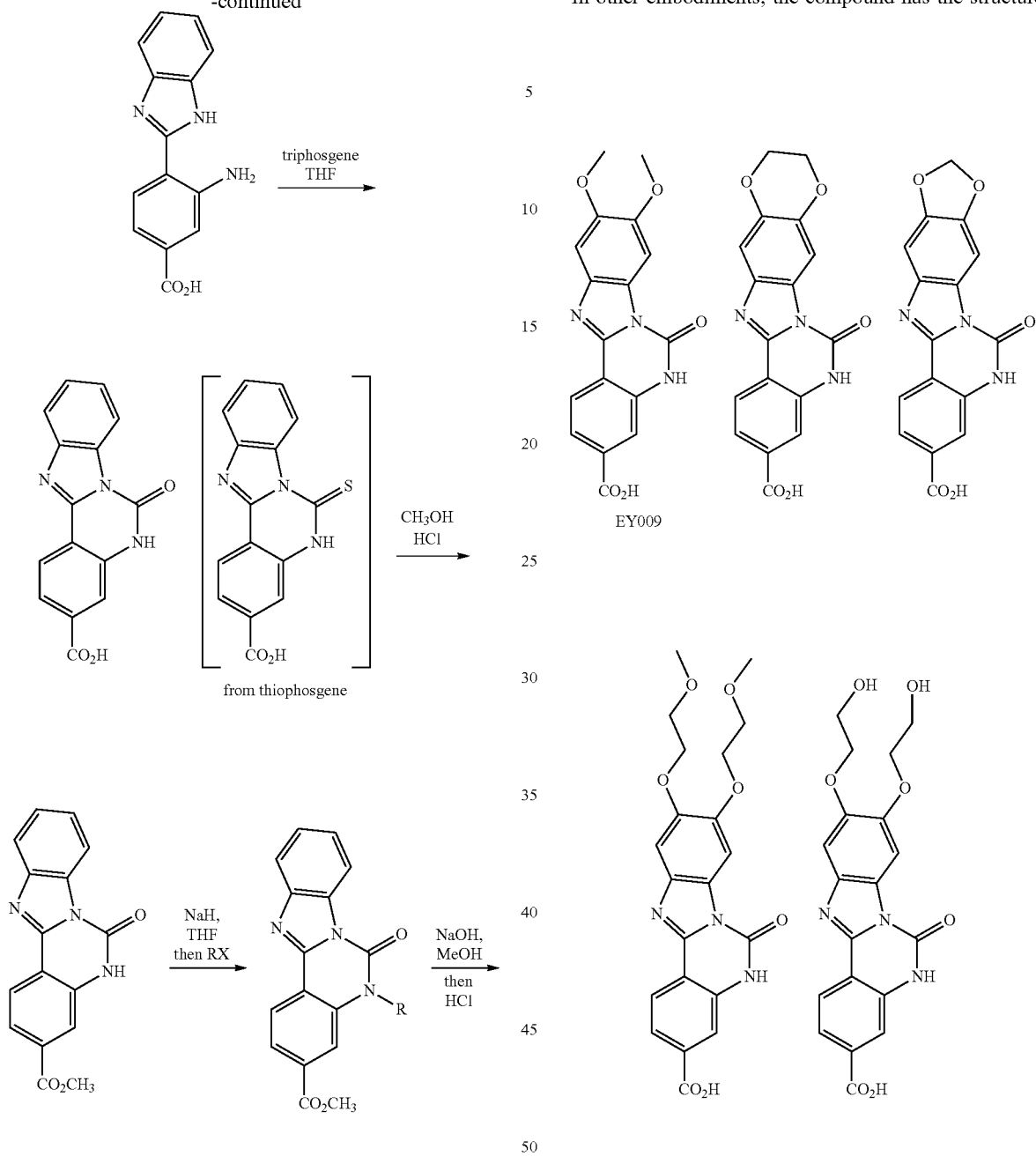
In other embodiments, the compound has the structure:
EY009
The compounds with the neutral solubilizing groups may be synthesized as shown in the following scheme:
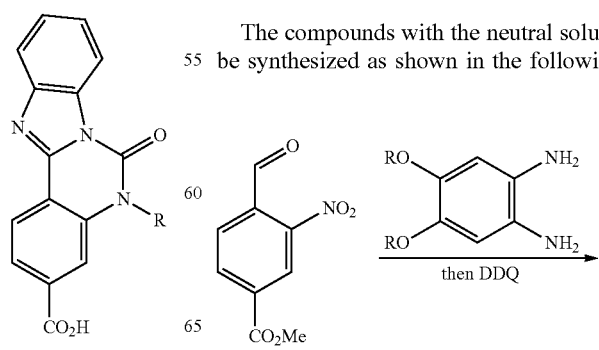

-continued
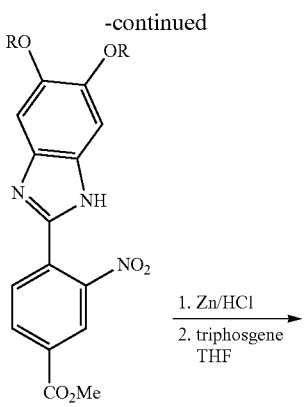
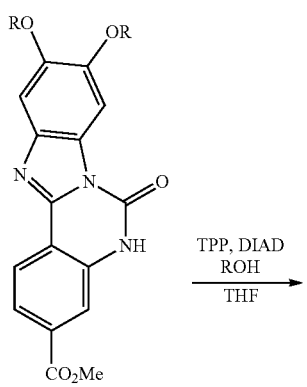
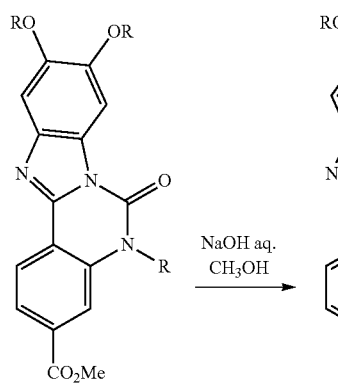
Alternatively, the compound may have groups that will ionize and become charged under physiologic conditions having the structure:
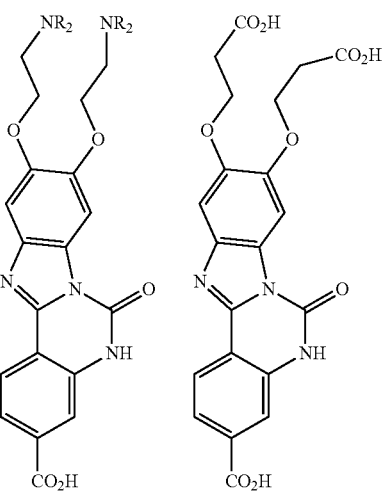
R = H, alkyl
The synthetic scheme to prepare the compounds with groups that will ionize may be prepared as follows:
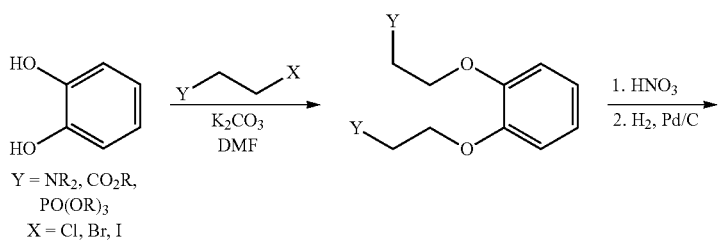
Y = NR$_2$, CO$_2$R, PO(OR)$_3$
X = Cl, Br, I

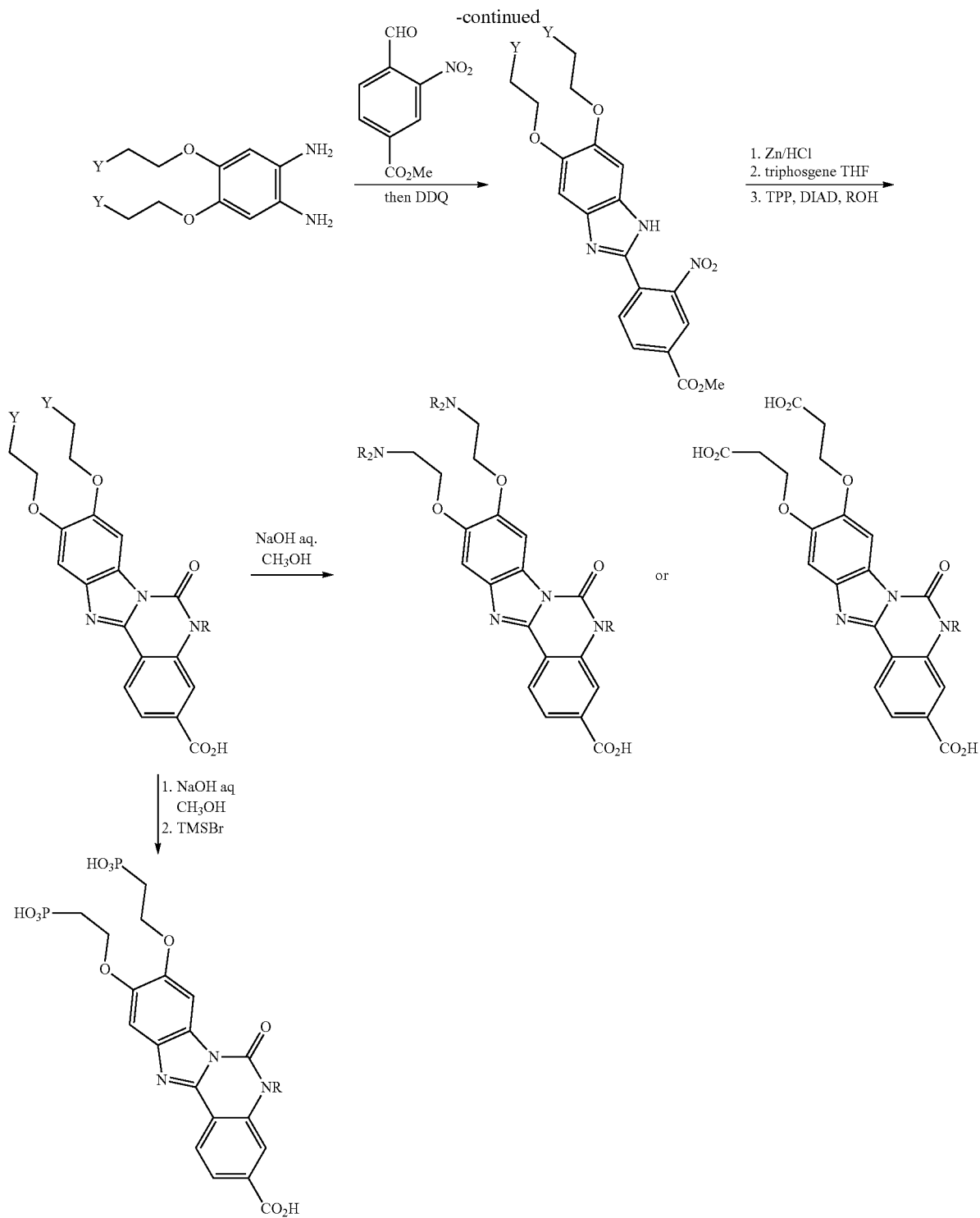

In some embodiments, the presently disclosed subject matter provides a pharmaceutical composition comprising, consisting of, or consisting essentially of a compound as described herein and a pharmaceutically acceptable carrier. Suitable carriers can include (but are not limited to) water, aqueous solution, polymer (such as hydroxypropyl methylcellulose), petrolatum, mineral oil, castor oil, carboxymethyl cellulose, organic liquid lipid, polyvinyl alcohol, hydroxypropyl cellulose, hyaluronic acid, glycerin, polyethylene glycol, polysorbate 80, povidone, and/or dextran. The disclosed compositions can be present in the carrier in an amount of from about 0.5-20 weight %, such as about 0.5-10%, 0.5-9%, 0.5-8%, 0.5-7%, 0.5-6%, 0.5-5%, 0.5-4%, 0.5-3%, 0.5-2%, or 0.5-1%, based on the total weight of the composition.

The disclosed compositions can optionally comprise one or more buffers, tonicity agents, preservatives, and/or chelating agents. Suitable buffers include (but are not limited to)

acetate, borate, carbonate, citrate, and/or phosphate buffers. Suitable tonicity agents that can be used to adjust the disclosed compositions to a desired isotonic range can include (but are not limited to) glycerin, mannitol, sorbitol, sodium chloride, and/or other electrolytes. Suitable preservatives that can be used to prevent bacterial contamination include (but are not limited to) polyhexamethylenebiguanidine (PHMB), benzalkonium chloride (BAK), stabilized oxychloro complexes (Purite®), phenylmercuric acetate, chlorobutanol, sorbic acid, chlorhexidine, benzyl alcohol, parabens, and/or thimerosal. Suitable chelating agents that can be used to enhance preservative effectiveness include (but are not limited to) edetate salts, such as edetate disodium, edetate calcium disodium, edetate trisodium, and/or edetate dipotassium.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Substitution with positron emitting isotopes, such as $^{11}$C, $^{18}$F, $^{15}$O and $^{13}$N, can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. Alternatively, deuterium may be also incorporated into a compound using methods such as through reduction such as using $LiAlD_4$ or $NaBD_3$, catalytic hydrogenation or acidic or basic isotopic exchange using appropriate deuterated reagents such as deuterides, $D_2$ and $D_2O$. In addition to the above, PCT publications, WO2014/169280; WO2015/058067; U.S. Pat. Nos. 8,354,557; 8,704,001 and US Patent Application Publication Nos.; 2010/0331540; 2014/0081019; 2014/0341994; 2015/0299166, the methods are hereby incorporated by reference.

In some embodiments, the pH of the disclosed compositions can be about 4 to 8, such as about 4.5-7.5, 4.5-6.5, or 4.5-5.5.

In some embodiments, the presently disclosed subject matter is directed to a method of modulating CaMKK2 activity in a cell. The method comprises, consists of, or consists essentially of administering an effective amount of a compound as provided herein to the cell, such that the CaMKK2 activity is modulated. The term "administering" as used herein refers to the dosage of a compound or composition, such as a single dose or multiple doses of the disclosed compounds. The method used to administer includes multiple routes of delivery, especially topical delivery to the eye. Additional routes of delivery for any number of disease indications include but are not limited to subconjunctival delivery, sub-Tenon's delivery, intracameral delivery, intravitreal delivery, suprachoroidal delivery, punctal delivery, retrobulbar delivery, intravenous delivery, subcutaneous delivery, intramuscular delivery, oral delivery, inhalational delivery, and intrathecal delivery.

The pharmaceutical compositions provided herein can be administered topically to the skin, orifices, or mucosa. The topical administration, as used herein, includes (intra)dermal, conjunctival, intracorneal, intraocular, ophthalmic, and transdermal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases. The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinyl-alcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

In some embodiments, the presently disclosed subject matter is directed to a method of inhibiting CaMKK2 activity in a target cell. The method comprises, consists of, or consists essentially of administering an effective amount of a compound as described herein to the cell such that the CaMKK2 activity is inhibited.

In some embodiments, the presently disclosed subject matter is directed to a method for treating an ocular indication in a subject. The method comprises, consists of, or consists essentially of administering to the subject an effective amount of a compound as described herein such that the ocular indication is treated. Typical ocular diseases include but are not limited to anterior segment or front-of-the-eye diseases (i.e., corneal and/or conjunctival diseases, such as aqueous tear deficiency, meibomian gland dysfunction, or OGVHD). Diseases can also include uveitis and other inflammatory diseases of the eye (i.e., iritis, iridocyclitis, intermediate uveitis, posterior uveitis, or panuveitis, of noninfectious, infectious, or idiopathic etiologies). Diseases can also include posterior segment or back-of-the-eye diseases (i.e., retinal and/or choroidal diseases, such as age-related macular degeneration (AMD), diabetic retinopathy, or retinal degeneration/dystrophy). In some embodiments, the ocular indication comprises one or more ocular diseases characterized by T cell and/or macrophage-mediated inflammation. In some embodiments, the disease is characterized by increased CaMKK2 activity.

In some embodiments, the "effective amount" (or "therapeutically effective amount") of a composition comprises an amount sufficient to effect beneficial or desirable biological and/or clinical results.

The term "subject" as used herein includes animals, such as mammals. Suitable subjects can include (but are not limited to) primates, cows, sheep, goats, dogs, cats, horses, rabbits, rats, mice, and the like. In some embodiments, the subject is a human.

The term "treated" or "treatment" as used herein refers to arresting or ameliorating a disease, disorder, or at least one of the clinical symptoms of a disease or disorder; reducing the risk of acquiring a disease, disorder, or at least one of the clinical symptoms of a disease or disorder; reducing the development of a disease, disorder or at least one of the clinical symptoms of the disease or disorder; and/or reducing the risk of developing a disease or disorder or at least one of the clinical symptoms of a disease or disorder. "Treated" or "treatment" can also refer to inhibiting a disease or disorder, either physically (e.g., stabilization of a discernible symptom), physiologically (e.g., stabilization of a physical parameter), or both, or inhibiting at least one physical parameter that may not be discernible to the subject. Further, "treated" or "treatment" can refer to delaying the onset of the disease or disorder or at least symptoms thereof in a subject that may be exposed to or predisposed to a disease or disorder, even though that subject does not yet experience or display symptoms of the disease or disorder.

In some embodiments, the presently disclosed subject matter is directed to a method of treating cancer in a subject. The method comprises, consists of, or consists essentially of administering an effective amount of a compound as described herein to the subject such that the cancer is treated. In some embodiments, the cancer is characterized by increased CaMKK2 activity within cancer cells or within infiltrating or accessory cells (i.e. vascular cells, immune cells, etc.) within or related to the cancer.

In some embodiments, the presently disclosed subject matter is directed to a method of treating a subject with a satiety-control disease. The method comprises, consists of, or consists essentially of administering an effective amount of a compound as described herein to a subject such that the satiety-control disease is treated.

Another aspect of the present disclosure provides all that is disclosed and illustrated herein.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Development of Novel Small Molecule Inhibitor Compounds

Computational modeling of the crystal structure of STO-609/CaMKK2 was used to develop a library of small molecule inhibitors of CaMMK2 (SMICs) based on computational chemistry. Particularly, the crystal structure of STO-609/CaMKK2 was obtained, portions of the tool compound not predicted to interfere with receptor binding but that should have improved solubility (calculated Log P ~3) without detrimental effects on cell penetration (total polar surface area <140 was considered favorable) were modified. Five (5) initial compounds were synthesized by MonomerChem (RTP, North Carolina) and were used to generate the data herein.

Table 1 below illustrates the initial 5 compounds synthesized, each of which is representative of a novel subclass.

TABLE 1
| Compounds 1-10 | | | |
|---|---|---|---|
| Compound ID # | Structure | cLogP | TPSA* |
| STO-609 |  | 3.74 | 71.7 |
| 1 (EY301) (EY1001.A001.B001) |  | 2.74 | 87.5 |
| 2 (EY302) (EY2001.A001.B001) |  | 3.08 | 70.5 |
| 3 (EY303) (EY1002.A001.B001) | 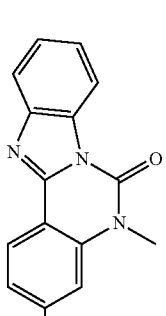 | 2.81 | 76.6 |

TABLE 1-continued

Compounds 1-10

| Compound ID # | Structure | cLogP | TPSA* |
|---|---|---|---|
| 4 (EY304) (EY1003.A001.B001) | 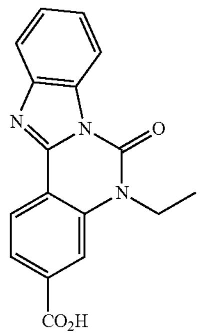 [SMILES: CCn1c(=O)n2c3ccccc3nc2c2ccc(C(=O)O)cc21] | 3.18 | 76.6 |
| 5 (EY305) (EY1004.A001.B001) | 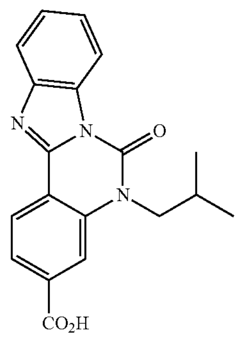 [SMILES: CC(C)Cn1c(=O)n2c3ccccc3nc2c2ccc(C(=O)O)cc21] | 3.93 | 76.6 |
| 6 (EY0001) (EY1005.A001.B001) | 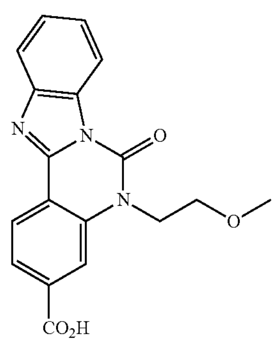 [SMILES: COCCn1c(=O)n2c3ccccc3nc2c2ccc(C(=O)O)cc21] | 2.79 | 85.8 |
| 7 (EY0007) (EY1006.A001.B001) | 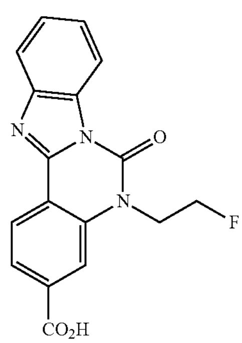 [SMILES: O=C(O)c1ccc2c(c1)n(CCF)c(=O)n1c3ccccc3nc21] | 3.10 | 76.6 |

TABLE 1-continued

Compounds 1-10

| Compound ID # | Structure | cLogP | TPSA* |
|---|---|---|---|
| 8 (EY0002) (EY1007.A001.B001) | 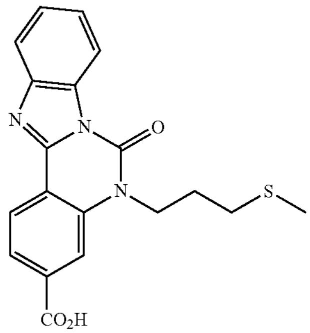 [SMILES: CSCCCn1c(=O)n2c3ccccc3nc2c2ccc(C(=O)O)cc21] | 3.60 | 76.6 |
| 9 (EY0006) (EY1008.A001.B001) | 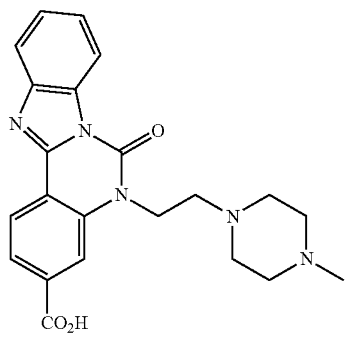 [SMILES: CN1CCN(CCn2c(=O)n3c4ccccc4nc3c3ccc(C(=O)O)cc32)CC1] | 2.73 | 83.1 |
| 10 (EY0009) (EY1001.A002.B001) | | 2.36 | 105.9 |

Example 2

Biochemical Activity Against CaMKK2

Figure 4A:
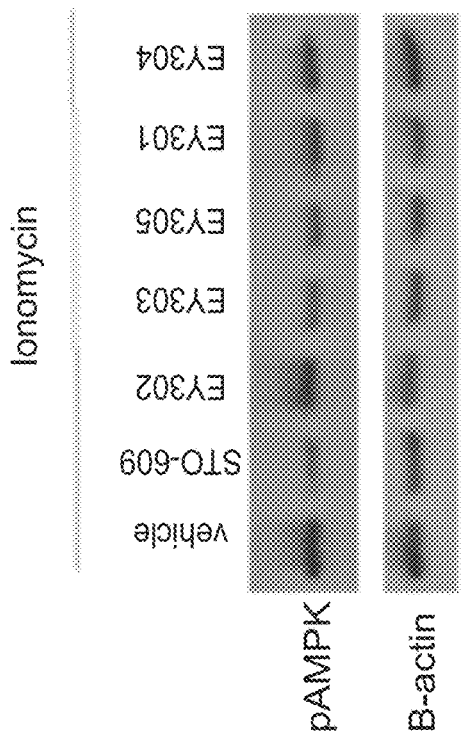
FIGS. 4A and 4B are Western blots illustrating inhibition of CaMKK2 enzymatic activity by (A) CaMKK2 auto-phosphorylation and (B) AMPK phosphorylation, by vehicle, small molecule compounds EYE301-EYE305, and tool compound STO-609, in cultured HEK293 cells.
Figure 4B:
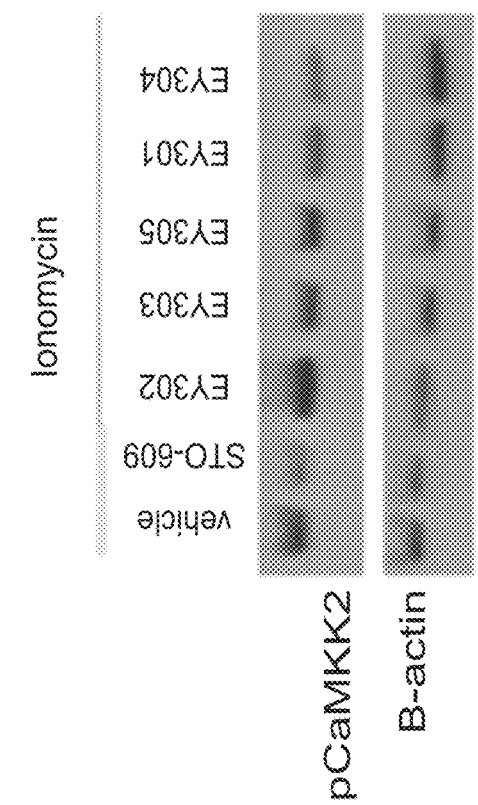
Figure 4C:
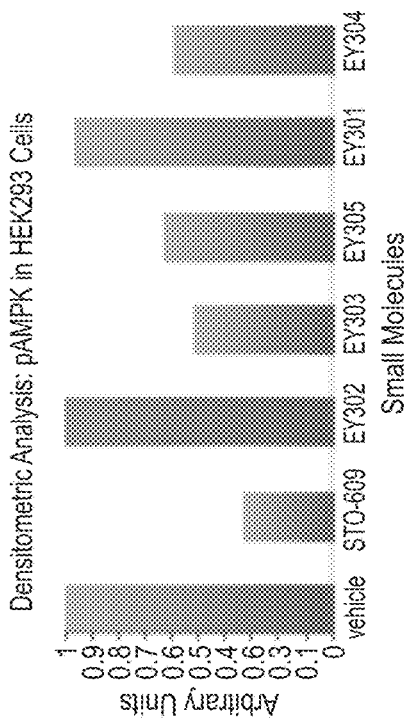
FIGS. 4C and 4D are bar graphs illustrating the densitometry analysis of Western blots, demonstrating inhibitory activity of CaMKK2 of C) CaMKK2 auto-phosphorylation and D) AMPK phosphorylation, by vehicle, small molecule compounds EYE301-EYE305, and tool compound STO-609, in cultured HEK293 cells.
Figure 4D:
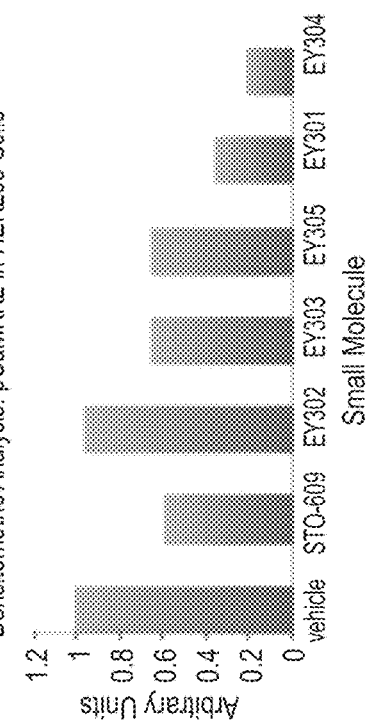

Preliminary screening of Compounds EY301-EY305 was performed in vitro in HEK293 cells (all tested at 10 μM). In brief, HEK293 cells were cultured to sub confluence in RPMI-40 complete media and 1% fetal bovine serum (FBS), incubated at 37° C. in 5% $CO_2$. Cultured cells were then switched to serum-free media overnight prior to initiation of experiments. Cells were then pre-treated with one of the five SMICs (EY301, EY302, EY303, EY304, and EY305, all at 10 μM concentration), STO-609 (10 μM), or vehicle control for 2 hours incubated at 37° C. in 5% $CO_2$. Cells were then stimulated with the calcium ionophore ionomycin (0.5 μg/mL) for 15 minutes, following which the cells were washed, harvested, and lysed for recovery of total protein using standard methods. Following standard protein gel electrophoresis, Western blot was then performed for either phospho-CaMKK2 (FIG. 4A) or phospho-AMPK (FIG. 4B) for each condition. Studies were performed in triplicate. Densitometry analysis demonstrated robust inhibition of CaMKK2 auto-phosphorylation (FIG. 4C) for EY301, EY303, EY304, and EY305 (with EY301 and EY304 appearing more effective as compared to STO-609) and partial inhibition of phospho-AMPK (FIG. 4D) for EY303, EY304, and EY305, all of which were comparable to STO-609.

Prophetic Example 3

Functional Screening of Compounds 1-5

Figure 5:
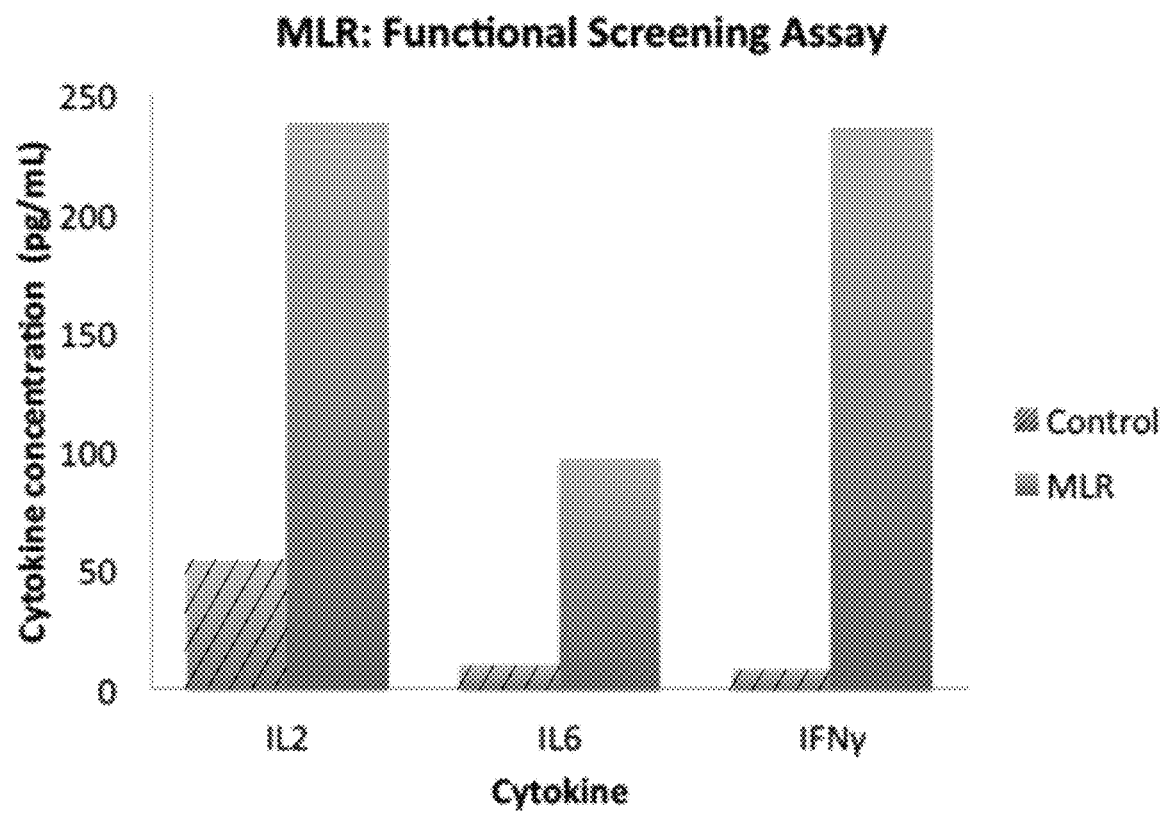
FIG. 5 is a bar graph illustrating measurement of pro-inflammatory cytokines in a mixed lymphocyte reaction, which can be used to screen functional inhibitory capacity of small molecule inhibitors of CaMKK2 (SMICs) in vitro (i.e. "GVHD in a dish").

A one-way mixed lymphocyte reaction (MLR) (FIG. 5) will be used to screen for functional inhibitory capacity of EY301-EY305. Spleen cells of C57BL/6 mice will be used as response cells, and the spleen cells of BALB/c mice (irradiated with Co60, 3000 rads) will be used as stimulator cells. The two types of cells are then mixed with equal volumes and concentrations and incubated at 37° C. in 5% $CO_2$ in low serum conditions for 24 hours, in the presence of 1) vehicle control; 2-6) one each of the five SMICs (EY301-EY305), or 7) STO-609, (at varying concentration 10 μM, 3 μM, 1 μM, 0.3 μM, and 0.1 μM for each SMIC or STO-609). Each concentration/condition will be performed in triplicate. The supernatant will then be recovered and concentrated for analysis by enzyme-linked immunosorbent assay (ELISA) for each of several key T cell- and macrophage-derived cytokines and effector molecules thought to mediate the destructive damage by infiltrating immune cells (e.g., TNF-α, IL-2, TGF-β, and IFN-γ). The functional inhibitory activity of EY301-EY305 will then be determined by calculation of the $IC_{50}$ of each compound for each cytokine of interest. The compounds will then be ranked ordered by $IC_{50}$ concentration for each cytokine of interest to assess the relative efficacy and potency of each SMIC for immune cell effector function.

Example 4

Mouse Model of OGVHD

Figure 6:
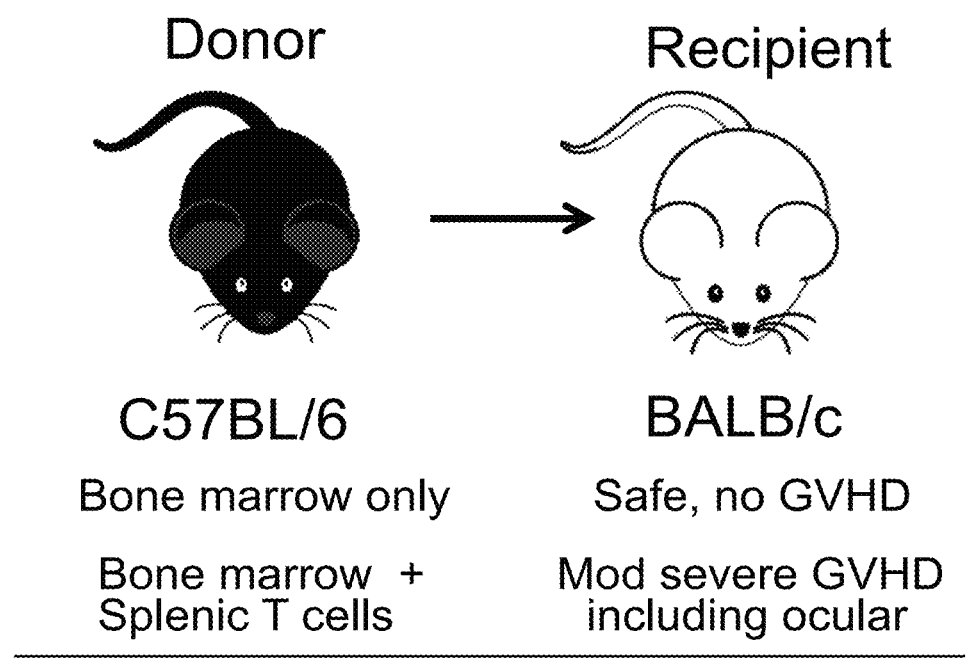
FIG. 6 is an illustration of a mouse model of graft-versus-host disease, based on bone marrow transplantation, with concurrent adoptive transfer of splenic T cells, from C57Bl/6 into BALB/c mice.

Ocular graft versus host disease (OGVHD), a disease in which T cells and macrophages are known to play key pathogenic roles, represents a model ocular inflammatory disease since A) it is known to share overlapping pathologic and clinical features with other, more common ocular inflammatory diseases (i.e. aqueous tear deficiency, meibomian gland dysfunction, uveitic disease, others); and B) the at-risk population is well defined since it occurs in individuals undergoing allogeneic bone marrow transplant for hematologic malignancies, autoimmune diseases, and other disorders. As such, experimental models of OGVHD represent attractive systems in which to study the therapeutic potential of targeting and inhibiting CaMKK2 for ophthalmic diseases. A mouse model based on bone marrow transplantation ("BMT") with supplementation of splenic T cells, from C57BL/6 into BALB/c mice, which represents a major histocompatibility mismatch, recapitulates key pathologic features of ocular graft versus host disease (OGVHD) (FIG. 6). In brief, 2-3-month old mice of C57BL/6 and BALB/c strains are used for this model. C57BL/6 mice are sacrificed, following which RPMI-1640 medium is flushed in the diaphyseal channel of both recovered tibias and femurs. Bone marrow is then homogenized and filtered, and unpurified bone marrow (BM) cells, devoid of red blood cells, are recovered from donor mice. Additionally, donor spleen is harvested aseptically, cut into small pieces, mashed with a spatula, and filtered and isolated to a single-cell suspension of isolated spleen-derived T cells. Recipient BALB/c mice undergo total body lethal irradiation at a dose of irradiated 950 cGy (with Cesium-137 source), following which donor C57BL/6 BM cells and spleen-derived T cells are transplanted to irradiated recipient mice via tail vein injection.

Figure 9A:
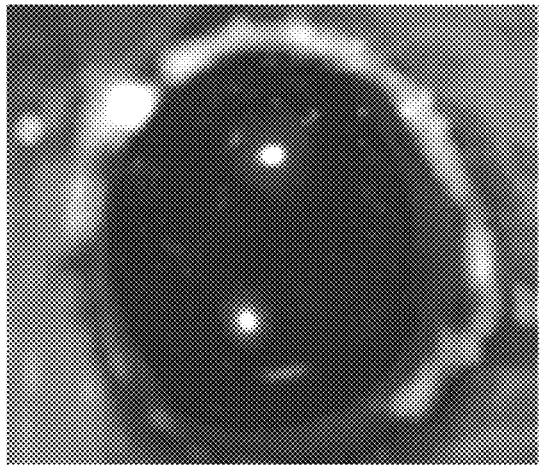
FIGS. 9A and 9B illustrates ocular surface fluorescein staining after A) control "safe" BMT and B) GVHD BMT (with concurrent adoptive transfer of splenic T cells).
Figure 9B:
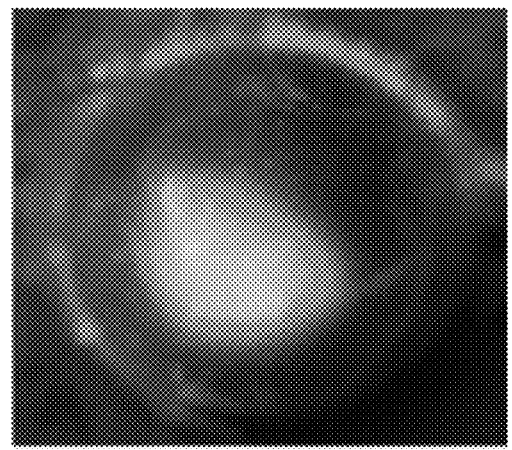
Figure 9C:
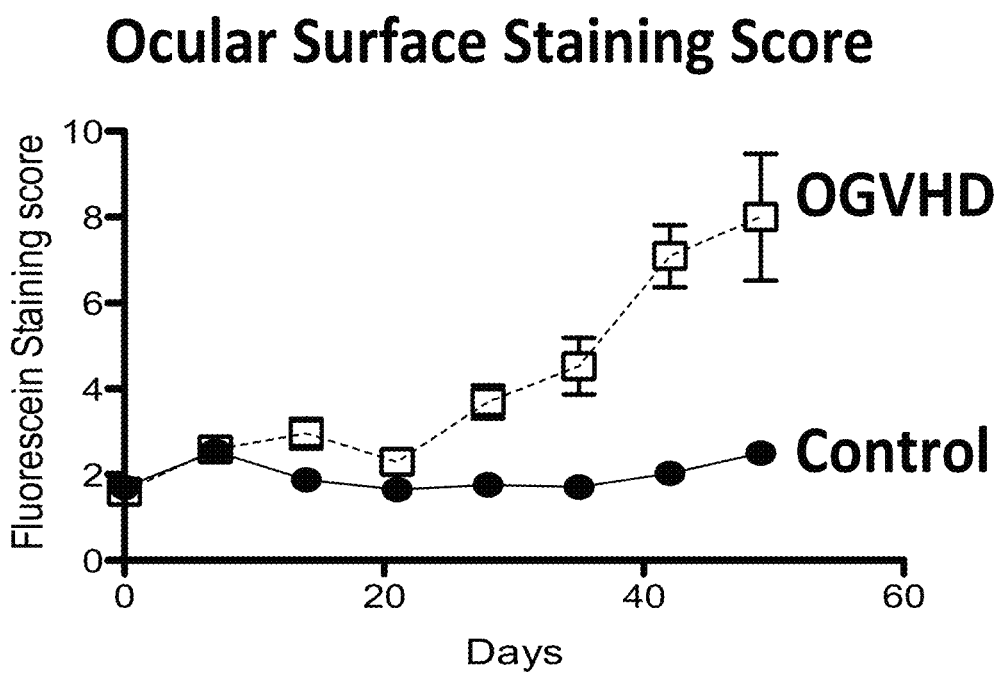
FIG. 9C is a plot of the ocular surface fluorescein staining scores of control safe BMT mice and GVHD BMT mice.

In the absence of concurrent adoptive transfer of spleen-derived T cells, clinical GVHD does not develop (FIG. 7A) (termed "safe BMT"). Clinical GVHD does develop when donor spleen-derived T cells are added to the bone marrow graft (GVHD BMT), and the relative severity of GVHD increases with increasing dose of transplanted spleen-derived T cells. Classic findings of severe human OGVHD, which include tearing, lid crusting, lid margin edema, chemosis, and keratopathy, are all observed in this model (FIG. 7B). OGVHD signs began to manifest within 14 days post BMT+T-cell adoptive transfer, progressing in severity over time (FIG. 8, GVHD BMT severity score at ~90 days, compared to safe BMT). Keratopathy is observed to be severe, as evidenced by intense fluorescein staining of the ocular surface (FIG. 9B), as compared to control safe BMT with no corneal staining (FIG. 9A) (Fluorescein staining quantified by a clinical grading system, described in (33). Quantitative scoring of these parameters, using a validated clinical grading system (34), demonstrated a mean clinical score of 24±2 in the BMT+T cell recipient group with experimental OGVHD (FIG. 9C), as compared to 4±2 in the control safe BMT recipient group without signs of OGVHD (FIG. 9C).

These clinical findings of OGVHD are associated with significant histopathologic evidence of T cell (FIG. 10A) and macrophage (FIG. 10B) infiltration into the corneal stroma as well as the bulbar and tarsal conjunctiva of affected mice. Collectively, these data demonstrate that this model recapitulates essential clinical and pathologic features of human OGVHD and therefore is an ideal experimental model for the testing of novel drugs for the treatment of OGVHD, especially novel SMIC drugs.

Example 5

Local Administration of CaMKK2 Inhibitor

The OGVHD model described in Example 4 was used to test whether local ocular administration of tool compound CaMKK2 inhibitor STO-609 (1.5 mg/mL) might prevent or ameliorate severity of experimental OGVHD. Following BMT+T cell transfer, recipient BALB/c mice were allowed to convalesce for 14 days prior to initiation of experimental procedures. Beginning at day 14 post-BMT+T cell transfer, STO-609 or vehicle was administered daily for 2 weeks, with regular examination occurring throughout the treatment period. At the conclusion of the treatment period, eyes were then graded (in masked fashion) for signs of OGVHD and scored according to a modified clinical grading system (33, 34). Mice were then sacrificed and eyes recovered for histologic analysis of ocular adnexal tissue (lids, conjunctiva) and anterior segment (conjunctiva, sclera, cornea), with pathologic assessment of OGVHD (i.e. immune cell infiltration, conjunctival scarring, goblet cell loss, Meibomian gland scarring, and lacrimal gland disruption/infiltration/scarring).

Figure 11C:
FIG. 11C is a scatter plot of the eye pathology scores from allogeneic BMT+splenic T cell transfer, following local ocular treatment with either vehicle control or STO-609.
Figure 11C:
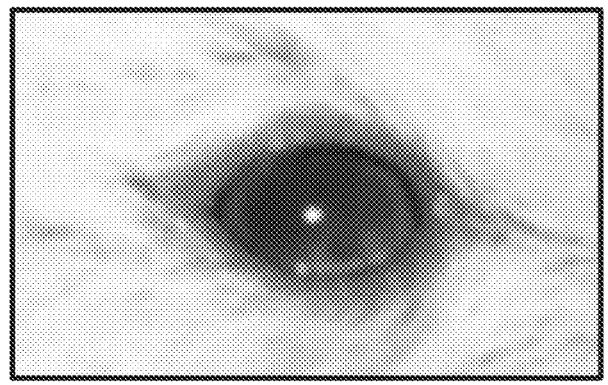
Figure 11C:
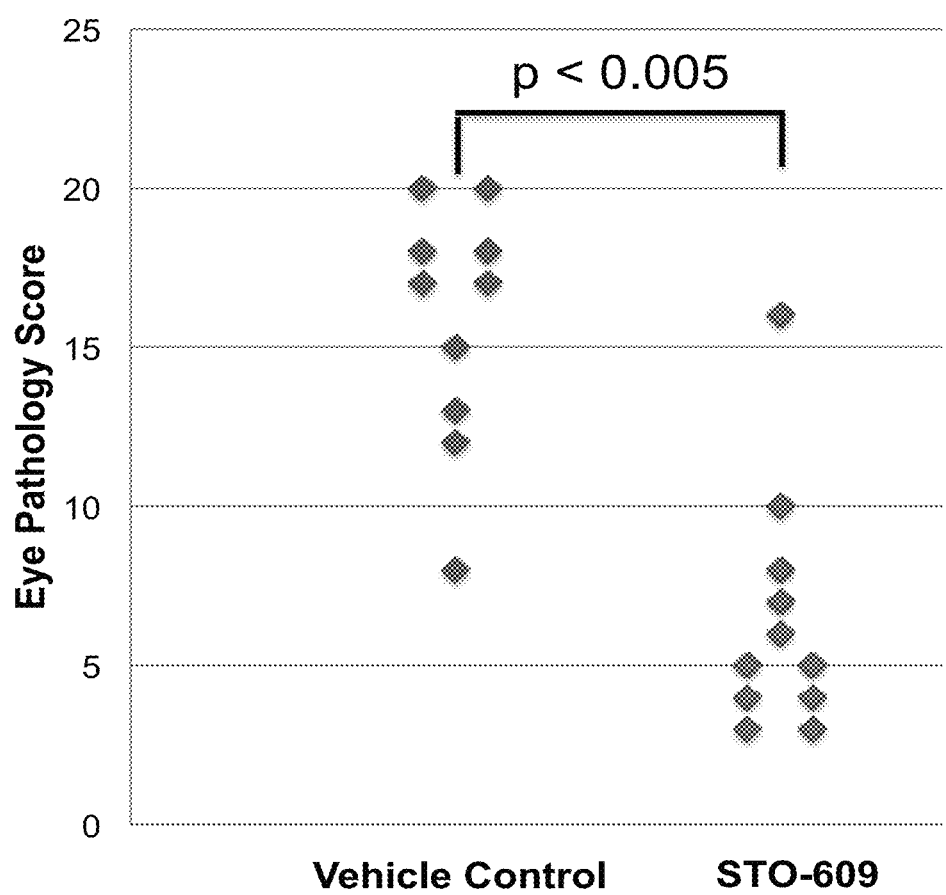

As compared to vehicle-treated mice, which had lid margin swelling and scarring with periocular fur loss, eyelid crusting, mild chemosis, decreased tear film, and keratopathy (FIG. 11A), STO-609 treated mice had fewer signs of OGVHD (FIG. 11B). The severity of OGVHD in STO-609 treated mice (median score 5) was significantly reduced as compared to vehicle-treated mice (median score 17) (FIG. 11C). Importantly, no apparent drug toxicity was observed. The results with the tool compound inhibitor STO-609 support CaMKK2 as a viable target for treatment of OGVHD and establish proof-of-concept for therapeutic potential of SMICs, providing a rational basis for in vivo testing of promising SMICs

Prophetic Example 6

Identification of SMIC that Suppresses T Cell and/or Macrophage Activity In Vitro We will identify at least one (1) SMIC from among a library of 20 NCE SMICs that suppresses T cell and/or macrophage activity in vitro and is efficacious in a mouse model of OGVHD. This will enable initial exclusion of compounds that do not have suppressive activity at high concentration in vitro. Using macrophage and T cell lines, capacity of candidate molecules to inhibit CaMKK2 activity will be assessed using Western blot densitometry analysis, phosphorylation of CaMKK2 substrates CaMKIV and AMPK as well as auto-phosphorylation of CaMKK2. Briefly, cells will be cultured in serum reduced conditions prior to treatment with 0.5 µg/mL ionomycin and 10 ng/mL PMA for 15 minutes, in the presence of vehicle, STO-609, candidate SMICs, or vehicle control. Cells will then be recovered and lysed for total protein, and Western blot analysis performed for pCaMKK2, pAMPK, pCaMKIV, with densitometry analysis normalized to actin, with SMICs inhibitory capacity compared to STO-609 and vehicle.

We will utilize a mixed lymphocyte reaction (MLR) (i.e. "GVHD in a dish") to rank order SMICs by potency of inhibition (i.e., $IC_{50}$) of T cell and macrophage effector function. The most promising SMICs (i.e. those with biochemical inhibitory activity) will be screened in an MLR assay to assess functional inhibition, specifically the reduction in production of inflammatory cytokines IL-2, TNF-α, IL-6, TGF-β, and IFN-γ by ELISA of MLR supernatant using three replicate assays. Using MLR data, SMICs will be rank ordered by $IC_{50}$ for each of the cytokines. Briefly, irradiated BALB/c splenocytes will be added to C57BL/6 splenocytes in triplicates for each condition: STO-609 and candidate SMICs (all at the following concentrations: 10 μM, 3 μM, 1 μM, 0.3 μM, and 0.1 μM) as well as vehicle control. ELISA will then be performed for inflammatory cytokines IL-2, TNF-α, IL-6, TGF-β, and IFN-γ with calculation of drug $IC_{50}$ for each cytokine. Measures of viability and apoptosis will also be performed for drug concentrations to ascertain potential dose-limiting toxicities in vitro.

A kinome scan will be performed to assess for off-target activity of candidate SMICs for >450 common kinases, using a commercially available fee-for-service technology available through eurofins/DiscoverX (Fremont, Calif.). The top 5 SMICs will be ranked according to least off-target activity. The goal of this collective screening strategy (Western blot analysis, MLR reaction, kinome scan) will be to nominate at least five (5)_SMICs, ranked by potency and lack of off-target activity, to advance to in vivo screening and testing.

Prophetic Example 7

In Vivo Tolerability of SMICs

We will perform nonGLP toxicology studies of top (5) SMICs administered topically in unmanipulated 2-3-month old wild-type BALB/c mice, assessing local toxicity by clinical assessment and by histopathology. In brief, 15 mM stock concentration in aqueous solvent will be used for each candidate SMIC, and preliminary dose ranging studies will be performed with 3-fold dilutions (3 doses, n=3 per dosing group, 5 candidate compounds) topically twice daily for 14 days, comparing to vehicle control (n=5). Local toxicity will be assessed with two metrics: (1) clinical findings (conjunctival hemorrhage, chemosis, corneal haze, inflammatory cells in AC), and (2) histology (cornea, conjunctiva, sclera, lens, retina, choroid). Following clinical biomicroscopic eye exam, mice will be sacrificed and eyes recovered for histology. Standard H&E sections of ocular tissue will be examined in a masked fashion for evidence of inflammation or tissue morphology change suggestive of toxicity. Superficial assessment for systemic toxicity will be performed, assessing failure to thrive and mortality. Any finding greater than "trace abnormal" will disqualify that compound concentration. The goal of these in vivo tolerability studies will be to identify at least two (2) SMICs with lack of ocular toxicity with topical application.

Prophetic Example 8

Proof-of-Concept in OGVHD

We will perform preclinical proof-of-concept studies in a mouse model of OGVHD to demonstrate the clinical efficacy of topical application of top two (2) SMIC candidates. Ultimately, the goal is to demonstrate that topical application of candidate SMICs reduces OGVHD severity, to establish proof-of-concept that selected SMICs could serve as therapeutics for not only OGVHD, but other more common ocular inflammatory disorders that share overlapping disease mechanisms with OGVHD. Preliminary data indicate that STO-609 achieves this goal, and these studies will affirm and extend to selected candidate SMICs. The two most promising candidate SMICs identified in Example 7 will be screened in this OGVHD model. Briefly, 2-3-month old mice of C57BL/6 and BALB/c strains are used for this model. C57BL/6 mice are sacrificed, following which RPMI-1640 medium is flushed in the diaphyseal channel of both recovered tibias and femurs. Recovered bone marrow is then homogenized and filtered, and unpurified bone marrow (BM) cells, devoid of red blood cells, are recovered from donor mice. Additionally, donor spleen is harvested aseptically, cut into small pieces, mashed with a spatula, and filtered to a single-cell suspension of isolated splenocytes, containing T cells. Recipient BALB/c mice undergo total body lethal irradiation at a dose of 950 cGy with Cesium-137 source, following which donor C57BL/6 BM cells and spleen-derived T cells are transplanted to irradiated recipient mice via tail vein injection. Recipient BALB/c mice will then be allowed to convalesce for approximately 14 days before initiation of further experimental procedures. At that time, twice-daily, bilateral topical treatment with selected drug will be initiated, with regular examination throughout a four-week treatment period. Clinical scoring will be performed after two weeks and four weeks of treatment. OGVHD clinical findings include lid margin edema, lid crusting, tear film disruption, conjunctival chemosis, and keratopathy. These findings will be graded using a quantitative scoring system adapted from previously published studies (33, 34). After the treatment period (six weeks post-BMT), mice will be sacrificed and eyes recovered for histologic analysis of ocular adnexal tissue (lids, conjunctiva) and anterior segment (conjunctiva, sclera, cornea), with pathologic assessment of OGVHD (i.e. immune cell infiltration, conjunctival scarring, goblet cell loss, Meibomian gland scarring, and lacrimal gland disruption/infiltration/scarring).

Treatment groups will be as follows:
a) Control Group: BL/6 donor BM without concurrent T cells (n=5) transplanted to BALB/c recipients (n=10), control group that does not develop OGVHD, no drug administered.
b) Exp. Group 1: BL/6 donor BM and T cells (n=8) transplanted to BALB/c recipients (n=15), vehicle control.
c) Exp. Group 2: BL/6 donor BM and T cells (n=8) transplanted to BALB/c recipients (n=15), STO-609.
d) Exp. Group 3: BL/6 donor BM and T cells (n=8) transplanted to BALB/c recipients (n=15). SMIC No. 1.
e) Exp. Group 4: BL/6 donor BM and T cells (n=8) transplanted to BALB/c recipients (n=15). SMIC No. 2.

For analysis of data and observed findings, nonparametric statistics (e.g. Mann-Whitney test) will be used to compare median scores among treatment groups, since clinical scoring reflects categorical grades. Parametric statistics will be used for comparison of continuous variables (e.g. quantitative immune cell infiltration) on pathologic assessment.

The goal of these studies will be to identify at least one candidate SMIC with 50% reduction in OGVHD score, as has been demonstrated and established for STO-609.

Example 9

Identification of SMIC that Suppresses Cellular CaMKK2 Activity In Vitro

The initial set of synthesized SMICs are referenced in Table 1. From among this set, six candidate SMICs (EY1003.A001.B001, EY1005.A001.B001, EY1006.A001.B001, EY1007.A001.B001, EY1008.A001.B001, EY1001.A002.B001) were selected for a cell-based biochemical screening assay in HEK293 cells. HEK-293 cells were treated with one of the following: STO-609, EY1003.A001.B001, EY1005.A001.B001, EY1006.A001.B001, EY1007.A001.B001, EY1008.A001.B001, EY1001.A002.B001 (all at 30 μM), or vehicle control, prior to stimulation with 1 mM ionomycin, a known activator of CaMKK2. Cell lysates were then probed by Western blot analysis with phospho-specific antibodies to CaMKK2 and AMPK, to assess effects of candidate SMICs on CaMKK2 auto-phosphorylation activity and substrate phosphorylation activity, respectively (FIG. 12). B-actin was included as a loading control. Graphs show quantification of relative densitometry, with signal normalized to B-actin to correct for protein loading variation across samples. Based on this analysis, candidate SMICs EY1006.A001.B001 and EY1001.A002.B001 demonstrated similar potency for CaMKK2 inhibitory activity, in vitro.

Example 10

In Vivo Tolerability of SMICs

NonGLP toxicology studies of locally administered candidate SMICs EY1006.A001.B001 and EY1001.A002.B001 was assessed in 2-3-month old wild-type BALB/c mice. assessing local toxicity by clinical assessment and by histopathology. Both compounds were topically administered at 1.5 mg/mL twice daily for 14 days. No signs of local toxicity were observed for either drug by clinical biomicroscopic eye examination or postmortem histologic assessment. Additionally, neither compound was associated with any apparent systemic toxicity (i.e., no evidence of failure to thrive or mortality).

Example 11

Proof-of-Concept in OGVHD

Preclinical proof-of-concept studies in a mouse model of OGVHD were performed to assess the clinical efficacy of topical administration of the two most promising candidate SMICs identified in Examples 6 and 7, EY1006.A001.B001 and EY1001.A002.B001. Previous experiments demonstrated that the tool compound inhibitor of CaMKK2 STO-609 achieves this goal, and the purpose of this study was to assess whether lead candidate NCE SMICs achieve comparable efficacy. Briefly, the OGVHD mouse model was initiated by isolation of bone marrow and splenic T cells from 2-3-month old mice C57BL/6J donor mice, and transplantation of isolated bone marrow and T cells to recipient 2-3-month old BALB/c mice, following ablation of recipient bone marrow. Recipient BALB/c mice were then allowed to convalesce for approximately 14 days before initiation of further experimental procedures. Mice were then treated with daily topical treatment with one of the following (experimental groups, n=5): STO-609 acetate (1.5 mg/mL), lead SMIC compounds EY1006.A001.B001 and EY1001.A002.B001 (both at 1.5 mg/mL), and 1% prednisolone acetate, beginning at day 14 post-BMT and continuing for two weeks.

OGVHD clinical findings include lid margin edema, lid crusting, tear film disruption, conjunctival chemosis, and keratopathy. These findings were clinically graded following one week and two weeks of treatment using a quantitative scoring system adapted from previously published studies (33, 34). Both lead SMICs EY1006.A001.B001 and EY1001.A002.B001 reduced severity of clinical OGVHD findings with efficacy similar to STO-609 (FIG. 13). By contrast, vehicle control-treated eyes had lid margin swelling and scarring with lash and periocular fur loss, eyelid crusting, chemosis, abnormal tear film, and keratopathy. STO-609 and lead SMICs were superior to vehicle and prednisolone, in preventing signs of OGVHD (p<0.05 for STO-609, EY1006.A001.B001, EY1001.A002.B001 vs vehicle or prednisolone). For this scoring system and experiment Mild disease was score 0-5, moderate disease was score 6-10 and severe disease was score >10.

The findings of this experiment establish proof-of-concept that selected SMICs with ideal physicochemical properties for topical administration may serve as therapeutics for OGVHD, as well as potentially more common ocular inflammatory disorders (i.e. inflammatory dry eye disorders) that share overlapping disease mechanisms with OGVHD.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

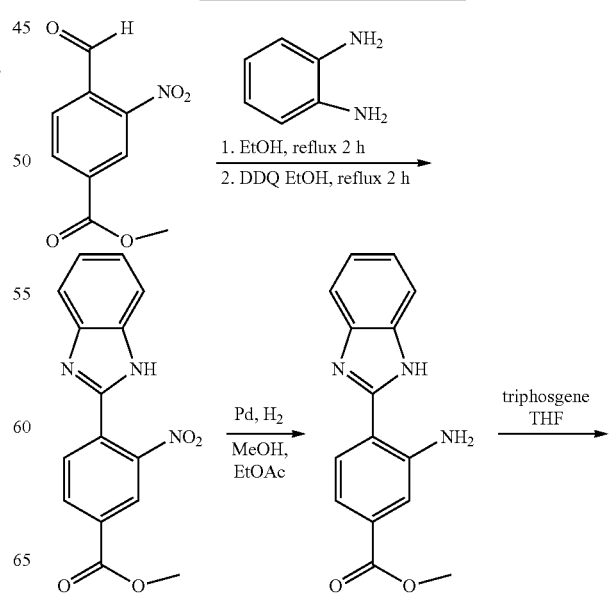

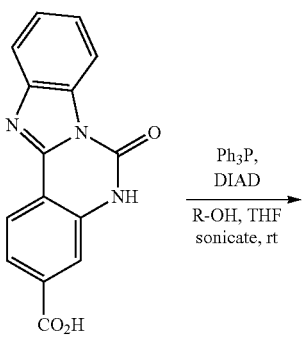

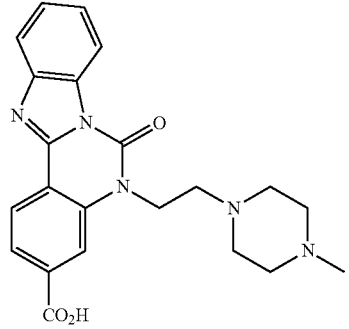

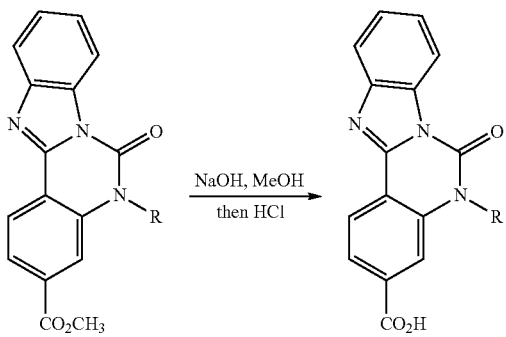

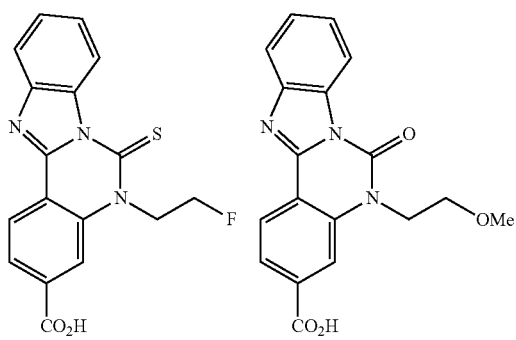

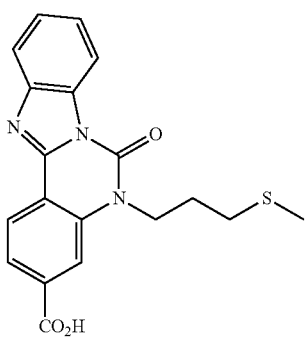

Compounds 6-9: General Procedure Step 1

An equimolar solution of the corresponding aldehyde and phenylenediamine (1 mmol) in EtOH (4 mL) was heated under reflux until all starting material was converted to the imine intermediate (ca.1.5 h). After addition of DDQ (395 mg, 1.1 mmol) the reaction mixture was heated at reflux until the imine intermediate was completely converted to the benzimidazole product (typically 30-60 min). The reaction mixture was then cooled to room temperature, diluted with saturated aqueous $NaHCO_3$, and the product was extracted twice with ethyl acetate. The combined organic extracts were dried with anhydrous MgSO4, filtered, and concentrated under reduced pressure. The crude product was purified by Flash column chromatography on silica to give the corresponding pure benzimidazole.

General Procedure Step 2.

A solution of nitro-substituted benzimidazole intermediate (2 g, 7 mmol) in 150 mL of methanol: ethyl acetate was hydrogenated at room temperature under ambient pressure in the presence of Pd on activated carbon catalyst (600 mg, 5 wt % Pd). After completion of the reaction (TLC), the catalyst was filtered off through a pad of Celite, and the filtrate was concentrated under reduced pressure providing the desired product as a yellow solid.

Compounds 6-9, General Procedure Step 3

To a solution of starting material aniline (7.5 mmol) in THF (100 mL) was added triphosgene (7.5 mmol. The mixture sonicated for 10 min and the resulting suspension was heated at 55-60° C. for 1 h. The mixture was concentrated to dryness. To the residue was added ice water and sat sodium bicarbonate. The solid formed was filtered. The solid was washed with water and dried and used it for the next reaction.

Compounds 6-9, General Procedure Step 4

A suspension of starting material urea (1.36 mmol), triphenylphosphine (6 mmol) and the alcohol (150 mL, excess) in THF 5 mL was sonicated for 5 min and was added diisopropyl azodicarboxylate (DIAD) 1.4 mL (7 mmol). The mixture was sonicated for 30 min. The mixture was stirred at room temperature overnight. The mixture was concentrated to dryness and the residue was diluted with diethyl ether. The precipitated solid was filtered and the solid was washed with dry ether (4×50 mL). The solid was dried and purified by flash chromatography (hexane-EtOAc, 0-50%) to furnish the desired compound.

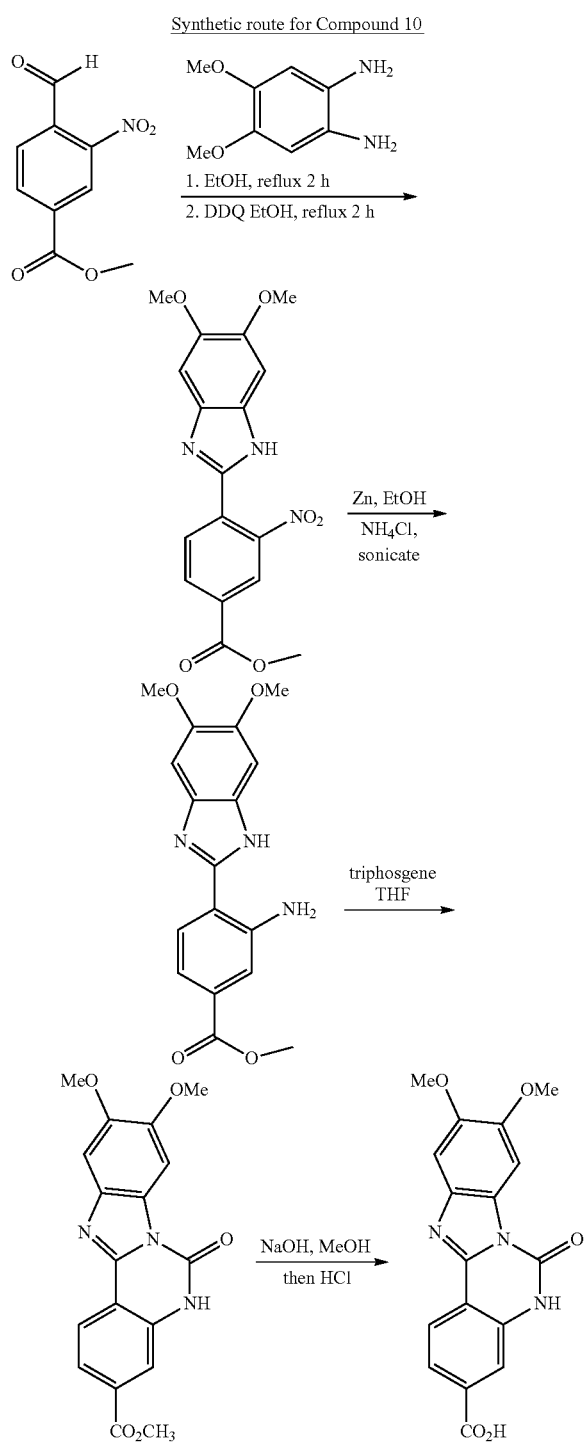

Synthetic route for Compound 10

Step 1: As Shown in the Procedure for Compounds 6-9, Step 1

Step 2: General Procedure:

To a solution of nitro compound (1 mmol) in ethanol 5 mL was added Zn powder (5 mmol) and saturated $NH_4Cl$ solution 2 mL. The mixture was sonicated for 2 h. The mixture was extracted with ethyl acetate (3×30 mL). The organic layer was washed with water, dried ($Na_2SO_4$) and concentrated to get a brown solid. The crude solid was purified by column chromatography (hexane-EtOAc, 0-100%) to furnish the desired product.

7. REFERENCES

The following references are incorporated herein in their entireties.

1. Tamas P, Hawley S A, Clarke R G, Mustard K J, Green K, Hardie D G, Cantrell D A. Regulation of the energy sensor AMP-activated protein kinase by antigen receptor and Ca2+ in T lymphocytes. J Exp Med. 2006; 203(7): 1665-70. doi: 10.1084/jem.20052469. PubMed PMID: 16818670; PMCID: PMC2118355.
2. Racioppi L, Means A R. Calcium/calmodulin-dependent kinase IV in immune and inflammatory responses: novel routes for an ancient traveler. Trends Immunol. 2008; 29(12):600-7. doi: 10.1016/j.it.2008.08.005. PubMed PMID: 18930438.
3. Racioppi L, Means A R. Calcium/calmodulin-dependent protein kinase kinase 2: roles in signaling and pathophysiology. J Biol Chem. 2012; 287(38):31658-65. doi: 10.1074/jbc.R112.356485. PubMed PMID: 22778263; PMCID: PMC3442500.
4. Racioppi L, Noeldner P K, Lin F, Arvai S, Means A R. Calcium/calmodulin-dependent protein kinase kinase 2 regulates macrophage-mediated inflammatory responses. J Biol Chem. 2012; 287(14):11579-91. doi: 10.1074/jbc.M111.336032. PubMed PMID: 22334678; PMCID: PMC3322820.
5. Blagih J, Coulombe F, Vincent E E, Dupuy F, Galicia-Vazquez G, Yurchenko E, Raissi T C, van der Windt G J, Viollet B, Pearce E L, Pelletier J, Piccirillo C A, Krawczyk C M, Divangahi M, Jones R G. The energy sensor AMPK regulates T cell metabolic adaptation and effector responses in vivo. Immunity. 2015; 42(1):41-54. doi: 10.1016/j.immuni.2014.12.030. PubMed PMID: 25607458.
6. Fracchia K M, Pai C Y, Walsh C M. Modulation of T Cell Metabolism and Function through Calcium Signaling. Front Immunol. 2013; 4:324. doi: 10.3389/fimmu.2013.00324. PubMed PMID: 24133495; PMCID: PMC3795426.
7. Izard J W, Kendall D A. Signal peptides: exquisitely designed transport promoters. Mol Microbiol. 1994; 13(5):765-73. PubMed PMID: 7815936.
8. Pan F, Means A R, Liu J O. Calmodulin-dependent protein kinase IV regulates nuclear export of Cabin1 during T-cell activation. EMBO J. 2005; 24(12):2104-13. doi: 10.1038/sj.emboj.7600685. PubMed PMID: 15902271; PMCID: PMC1150881.
9. Koga T, Otomo K, Mizui M, Yoshida N, Umeda M, Ichinose K, Kawakami A, Tsokos G C. Calcium/Calmodulin-Dependent Kinase IV Facilitates the Recruitment of Interleukin-17-Producing Cells to Target Organs Through the CCR6/CCL20 Axis in Th17 Cell-Driven Inflammatory Diseases. Arthritis Rheumatol. 2016; 68(8):1981-8. doi: 10.1002/art.39665. PubMed PMID: 26945541; PMCID: PMC4963275.
10. Naz H, Islam A, Ahmad F, Hassan M I. Calcium/calmodulin-dependent protein kinase IV: A multifunctional enzyme and potential therapeutic target. Prog Biophys Mol Biol. 2016; 121(1):54-65. doi: 10.1016/j.pbiomolbio.2015.12.016. PubMed PMID: 26773169.
11. Lento W, Huang W, Doan P, Chao N J, Racioppi L. Calcium Calmodulin Dependent Kinase Kinase 2 Regulates Hematopoietic Stem Cell Regeneration and Quiescence. Blood. 2014; 124(21):1571-.

12. Obba S, Hizir Z, Boyer L, Selimoglu-Buet D, Pfeifer A, Michel G, Hamouda M A, Goncalves D, Cerezo M, Marchetti S, Rocchi S, Droin N, Cluzeau T, Robert G, Luciano F, Robaye B, Foretz M, Viollet B, Legros L, Solary E, Auberger P, Jacquel A. The PRKAA1/AMPKalpha1 pathway triggers autophagy during CSF1-induced human monocyte differentiation and is a potential target in CMML. Autophagy. 2015; 11(7):1114-29. Epub 2015/06/02. doi: 10.1080/15548627.2015.1034406. PubMed PMID: 26029847; PMCID: PMC4590592.

13. Ogawa Y, Kim S K, Dana R, Clayton J, Jain S, Rosenblatt M I, Perez V L, Shikari H, Riemens A, Tsubota K. International Chronic Ocular Graft-vs-Host-Disease (GVHD) Consensus Group: proposed diagnostic criteria for chronic GVHD (Part I). Sci Rep. 2013; 3:3419. doi: 10.1038/srep03419. PubMed PMID: 24305504; PMCID: PMC3851919.

14. Ogawa Y, Shimmura S, Dogru M, Tsubota K. Immune processes and pathogenic fibrosis in ocular chronic graft-versus-host disease and clinical manifestations after allogeneic hematopoietic stem cell transplantation. Cornea. 2010; 29 Suppl 1:S68-77. doi: 10.1097/ICO.0b013e3181ea9a6b. PubMed PMID: 20935546.

15. Shikari H, Antin J H, Dana R. Ocular graft-versus-host disease: a review. Surv Ophthalmol. 2013; 58(3):233-51. doi: 10.1016/j.survophthal.2012.08.004. PubMed PMID: 23541042.

16. Caicedo A, Espinosa-Heidmann D G, Hamasaki D, Pina Y, Cousins S W. Photoreceptor synapses degenerate early in experimental choroidal neovascularization. J Comp Neurol. 2005; 483(3):263-77. doi: 10.1002/cne.20413. PubMed PMID: 15682400.

17. Caicedo A, Espinosa-Heidmann D G, Pina Y, Hernandez E P, Cousins S W. Blood-derived macrophages infiltrate the retina and activate Muller glial cells under experimental choroidal neovascularization. Exp Eye Res. 2005; 81(1):38-47. doi: 10.1016/j.exer.2005.01.013. PubMed PMID: 15978253.

18. Hsu L S, Tsou A P, Chi C W, Lee C H, Chen J Y. Cloning, expression and chromosomal localization of human Ca2+/calmodulin-dependent protein kinase kinase. J Biomed Sci. 1998; 5(2):141-9. Epub 1998/07/14. PubMed PMID: 9662074.

19. Anderson K A, Ribar T J, Lin F, Noeldner P K, Green M F, Muehlbauer M J, Witters L A, Kemp B E, Means A R. Hypothalamic CaMKK2 contributes to the regulation of energy balance. Cell Metab. 2008; 7(5):377-88. Epub 2008/05/08. doi: 10.1016/j.cmet.2008.02.011. PubMed PMID: 18460329.

20. Frigo D E, Howe M K, Wittmann B M, Brunner A M, Cushman I, Wang Q, Brown M, Means A R, McDonnell D P. CaM kinase kinase beta-mediated activation of the growth regulatory kinase AMPK is required for androgen-dependent migration of prostate cancer cells. Cancer Res. 2011; 71(2):528-37. doi: 10.1158/0008-5472.CAN-10-2581. PubMed PMID: 21098087; PMCID: PMC3074523.

21. Racioppi L. CaMKK2: a novel target for shaping the androgen-regulated tumor ecosystem. Trends Mol Med. 2013; 19(2):83-8. Epub 2013/01/22. doi: 10.1016/j.molmed.2012.12.004. PubMed PMID: 23332598; PMCID: PMC3565098.

22. Balasubramaniam S C, Raja H, Nau C B, Shen J F, Schornack M M. Ocular Graft-Versus-Host Disease: A Review. Eye Contact Lens. 2015; 41(5):256-61. doi: 10.1097/ICL.0000000000000150. PubMed PMID: 26214529.

23. Flowers M E, Martin P J. How we treat chronic graft-versus-host disease. Blood. 2015; 125(4):606-15. doi: 10.1182/blood-2014-08-551994. PubMed PMID: 25398933; PMCID: PMC4304105.

24. Nassiri N, Eslani M, Panahi N, Mehravaran S, Ziaei A, Djalilian A R. Ocular graft versus host disease following allogeneic stem cell transplantation: a review of current knowledge and recommendations. J Ophthalmic Vis Res. 2013; 8(4):351-8. PubMed PMID: 24653823; PMCID: PMC3957042.

25. Thanarajasingam G, Kim H T, Cutler C, Ho V T, Koreth J, Alyea E P, Antin J H, Soiffer R J, Armand P. Outcome and prognostic factors for patients who relapse after allogeneic hematopoietic stem cell transplantation. Biol Blood Marrow Transplant. 2013; 19(12):1713-8. doi: 10.1016/j.bbmt.2013.09.011. PubMed PMID: 24076323; PMCID: PMC3848699.

26. Bose T, Lee R, Hou A, Tong L, Chandy K G. Tissue resident memory T cells in the human conjunctiva and immune signatures in human dry eye disease. Sci Rep. 2017; 7:45312. doi: 10.1038/srep45312. PubMed PMID: 28345628; PMCID: PMC5366884.

27. Bron A J, Tomlinson A, Foulks G N, Pepose J S, Baudouin C, Geerling G, Nichols K K, Lemp M A. Rethinking dry eye disease: a perspective on clinical implications. Ocul Surf. 2014; 12(2 Suppl):S1-31. doi: 10.1016/j.jtos.2014.02.002. PubMed PMID: 24725379.

28. Dohlman T H, Ding J, Dana R, Chauhan S K. T Cell-Derived Granulocyte-Macrophage Colony-Stimulating Factor Contributes to Dry Eye Disease Pathogenesis by Promoting CD11b+ Myeloid Cell Maturation and Migration. Invest Ophthalmol Vis Sci. 2017; 58(2):1330-6. doi: 10.1167/iovs.16-20789. PubMed PMID: 28241321; PMCID: PMC5341624.

29. Pflugfelder S C, Karpecki P M, Perez V L. Treatment of blepharitis: recent clinical trials. Ocul Surf. 2014; 12(4):273-84. doi: 10.1016/j.jtos.2014.05.005. PubMed PMID: 25284773.

30. Tokumitsu H, Inuzuka H, Ishikawa Y, Ikeda M, Saji I, Kobayashi R. STO-609, a specific inhibitor of the Ca(2+)/calmodulin-dependent protein kinase kinase. J Biol Chem. 2002; 277(18):15813-8. doi: 10.1074/jbc.M201075200. PubMed PMID: 11867640.

31. Tokumitsu H, Inuzuka H, Ishikawa Y, Kobayashi R. A single amino acid difference between alpha and beta Ca2+/calmodulin-dependent protein kinase kinase dictates sensitivity to the specific inhibitor, STO-609. J Biol Chem. 2003; 278(13):10908-13. doi: 10.1074/jbc.M213183200. PubMed PMID: 12540834.

32. Monteiro P, Gilot D, Langouet S, Fardel O. Activation of the aryl hydrocarbon receptor by the calcium/calmodulin-dependent protein kinase kinase inhibitor 7-oxo-7H-benzimidazo[2,1-a]benz[de]isoquinoline-3-carboxylic acid (STO-609). Drug Metab Dispos. 2008; 36(12):2556-63. doi: 10.1124/dmd.108.023333. PubMed PMID: 18755850.

33. Perez V L, Barsam A, Duffort S, Urbieta M, Barreras H, Lightbourn C, Komanduri K V, Levy R B. Novel Scoring Criteria for the Evaluation of Ocular Graft-versus-Host Disease in a Preclinical Allogeneic Hematopoietic Stem Cell Transplantation Animal Model. Biol Blood Marrow Transplant. 2016; 22(10):1765-72. doi: 10.1016/j.bbmt.2016.07.012. PubMed PMID: 27492793; PMCID: PMC5580988.

34. Ahadome S D, Mathew R, Reyes N J, Mettu P S, Cousins S W, Calder V L, Saban D R. Classical dendritic cells mediate fibrosis directly via the retinoic acid pathway in severe eye allergy. JCI Insight. 2016; 1(12). doi: 10.1172/jci.insight.87012. PubMed PMID: 27595139; PMCID: PMC5004741.

8. GENERALIZED STATEMENTS OF THE DISCLOSURE

The following numbered statements provide a general description of the disclosure and are not intended to limit the appended claims.

Statement 1: A compound comprising Formula (I):

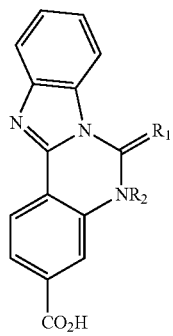

Formula (I)

or a pharmaceutically acceptable salt, solvate, hydrate, or derivative thereof, wherein $R_1$ is selected from oxygen (O) or sulfur (S); and wherein $R_2$ is selected from hydrogen (H), an alkyl, heteroalkyl, cycloalkyl, heterocycloalkyl, aryl, or heteroaryl group.

Statement 2. A compound comprising Formula (I):

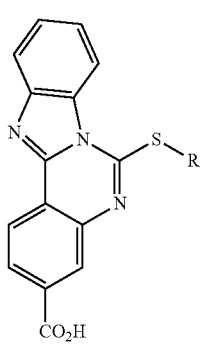

Formula (I)

or a pharmaceutically acceptable salt, solvate, hydrate, or derivative thereof, wherein R is selected from an alkyl, heteroalkyl, cycloalkyl, heterocycloalkyl, aryl, or heteroaryl group.

Statement 3. A compound comprising Formula (I) or Formula (II):

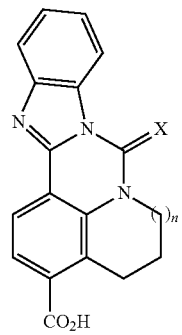

Formula (I)

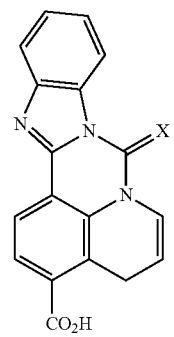

Formula (II)

or a pharmaceutically acceptable salt, solvate, hydrate, or derivative thereof, and wherein X is oxygen (O) or sulfur (S), and n is 1 or 2.

Statement 4. A compound comprising Formula (I):

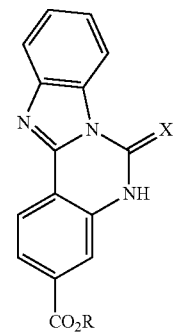

Formula (I)

or a pharmaceutically acceptable salt, solvate, hydrate, or derivative thereof, wherein X is oxygen (O) or sulfur (S), and R is an ester or ester prodrug comprised of but not limited to an alkyl, heteroalkyl, cycloalkyl, heterocycloalkyl, aryl, or heteroaryl group.

Statement 5. A compound comprising Formula (I):

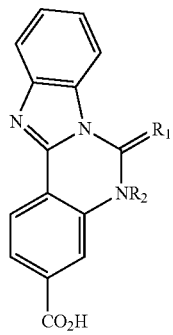

Formula (I)

or a pharmaceutically acceptable salt, solvate, hydrate, or derivative thereof, wherein X is oxygen (O) or sulfur (S);

wherein $R_1$ is selected from hydrogen (H), an alkyl, heteroalkyl, cycloalkyl, heterocycloalkyl, aryl, or heteroaryl group;

wherein $R_2$ is selected from hydrogen (H), an alkyl, heteroalkyl, cycloalkyl, heterocycloalkyl, aryl, or heteroaryl group.

Statement 6. A compound comprising Formula (I), (II), (III), or (IV):

Formula (I)

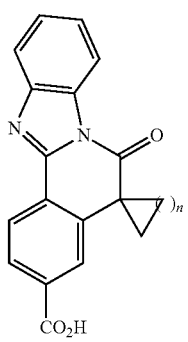

Formula (II)

Formula (III)

Formula (IV)

or a pharmaceutically acceptable salt, solvate, hydrate, or derivative thereof, wherein R, $R_1$, and $R_2$ are selected from an alkyl, heteroalkyl, cycloalkyl, heterocycloalkyl, aryl, or heteroaryl group; and wherein n is 1, 2, or 3.

Statement 7. A compound comprising Formula (I):

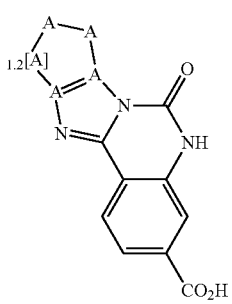

(Formula I)

wherein A denotes an atom in a carbocyclic or heterocyclic aromatic ring or a pharmaceutically acceptable salt, solvate, hydrate, or derivative thereof.

Statement 8. A compound comprising Formula (I):

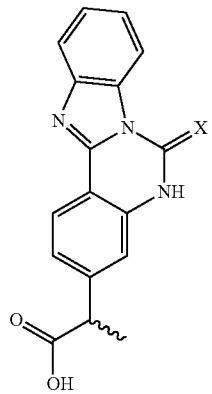

Formula (I)

or a pharmaceutically acceptable salt, solvate, hydrate, or derivative thereof, wherein X is oxygen (O) or sulfur (S).

Statement 9. A composition comprising Formula (I) or Formula (II):

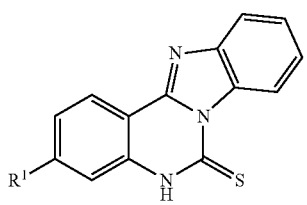

7,8

Formula (I)

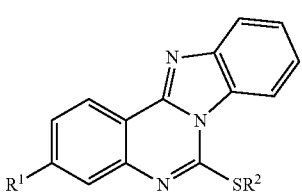

9-14

Formula (II)

or a pharmaceutically acceptable salt, solvate, hydrate, prodrug, or derivative thereof, wherein $R_1$ is hydrogen (H) or $COOCH_3$, and wherein $R_2$ is $CH_2CN$, $CH_2COOC_2H_5$, or $CH_2COPh$.

Statement 10. A method of modulating CaMKK2 in a subject, the method comprising administering an effective amount of the composition of Formula (I) to a subject:

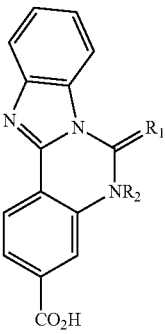

Formula (I)

or a pharmaceutically acceptable salt, solvate, hydrate, or derivative thereof, wherein $R_1$ is selected from oxygen (O) or sulfur (S); and wherein $R_2$ is selected from hydrogen (H), an alkyl, heteroalkyl, cycloalkyl, heterocycloalkyl, aryl, or heteroaryl group.

Statement 11. A method of modulating CaMKK2 in a subject, the method comprising administering an effective amount of the composition of Formula (I) to a subject:

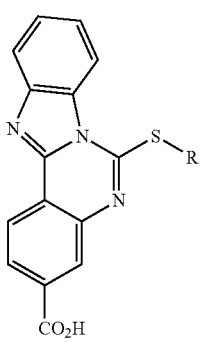

Formula (I)

or a pharmaceutically acceptable salt, solvate, hydrate, or derivative thereof, wherein R is selected from analkyl, heteroalkyl, cycloalkyl, heterocycloalkyl, aryl, or heteroaryl group.

Statement 12. A method of modulating CaMKK2 in a subject, the method comprising administering an effective amount of the composition of Formula (I), Formula (II), or both to a subject:

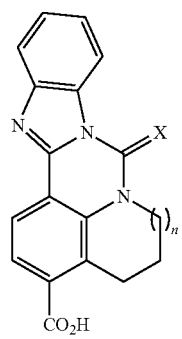

Formula (I)

-continued

Formula (II)

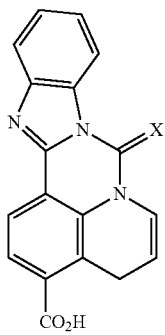

or a pharmaceutically acceptable salt, solvate, hydrate, or derivative thereof, wherein X is oxygen (O) or sulfur (S), and n is 1 or 2.

Statement 13. A method of modulating CaMKK2 in a subject, the method comprising administering an effective amount of the composition of Formula (I) to a subject:

Formula (I)

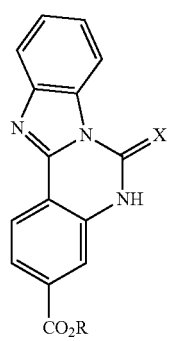

or a pharmaceutically acceptable salt, solvate, hydrate, or derivative thereof, wherein X is oxygen (O) or sulfur (S), and R is an ester or ester prodrug comprised of but not limited to an, cycloalkyl, heterocycloalkyl, aryl, or heteroaryl group.

Statement 14. A method of modulating CaMKK2 in a subject, the method comprising administering an effective amount of the composition of Formula (I) to a subject:

Formula (I)

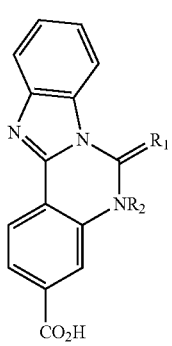

or a pharmaceutically acceptable salt, solvate, hydrate, or derivative thereof, wherein X is oxygen (O) or sulfur (S); wherein $R_1$ is selected from hydrogen (H), an, cycloalkyl, heterocycloalkyl, aryl, or heteroaryl group; and wherein $R_2$ is selected from hydrogen (H), cycloalkyl, heterocycloalkyl, aryl, or heteroaryl group.

Statement 15. A method of modulating CaMKK2 in a subject, the method comprising administering an effective amount of the composition of Formula (I), Formula (II), Formula (III), Formula (IV), or combinations thereof to a subject:

Formula (I)

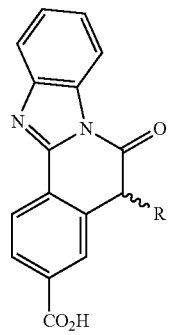

Formula (II)

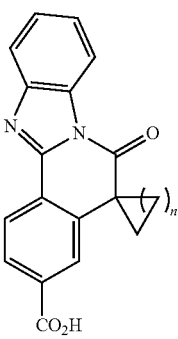

Formula (III)

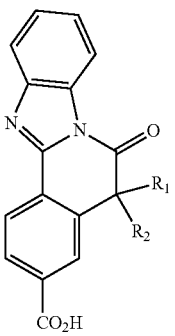

Formula (IV)

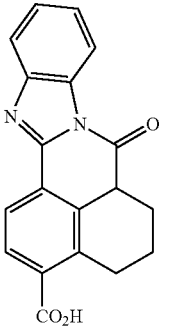

or a pharmaceutically acceptable salt, solvate, hydrate, or derivative thereof, wherein R, $R_1$, and $R_2$ are selected from an, cycloalkyl, heterocycloalkyl, aryl, or heteroaryl group; and wherein n is 1, 2, or 3.

Statement 16. A method of modulating CaMKK2 in a subject, the method comprising administering an effective amount of the composition of Formula (I) to a subject:

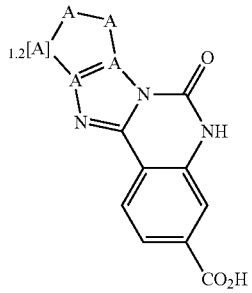

(Formula I)

wherein A denotes an atom in a carbocyclic or heterocyclic aromatic ring or a pharmaceutically acceptable salt, solvate, hydrate, or derivative thereof.

Statement 17. A method of modulating CaMKK2 in a subject, the method comprising administering an effective amount of the composition of Formula (I) to a subject:

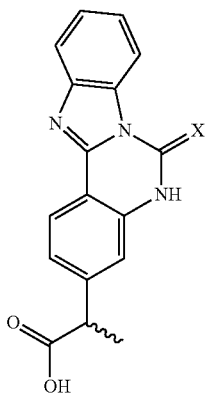

Formula (I)

or a pharmaceutically acceptable salt, solvate, hydrate, or derivative thereof, wherein X is oxygen (O) or sulfur (S).

18. A method of modulating CaMKK2 in a subject, the method comprising administering an effective amount of the composition of Formula (I), Formula (II), or both to a subject:

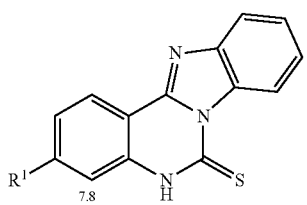

Formula (I)

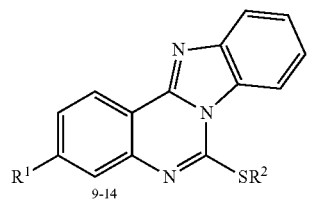

Formula (II)

or a pharmaceutically acceptable salt, solvate, hydrate, prodrug, or derivative thereof, wherein $R_1$ is hydrogen (H) or $COOCH_3$, and wherein $R_2$ is $CH_2CN$, $CH_2COOC_2H_5$, or $CH_2COPh$.

Statement 19. A method of treating any ophthalmic disease, which includes but is not limited to: 1) ocular surface inflammatory diseases (OSIDs), including but not limited to ocular graft versus host disease, ocular cicatricial pemphigoid, vernal keratoconjunctivitis, allergic eye disease, meibomian gland dysfunction, aqueous tear deficiency (common dry eye disease), corneal scarring, and conjunctival scarring and fibrosis; 2) uveitis and other inflammatory diseases of the eye, including but not limited to keratitis, scleritis, iritis, iridocyclitis, intermediate uveitis, pars planitis, posterior uveitis, choroiditis, chorioretinitis, retinitis, or panuveitis of noninfectious, infectious, or idiopathic etiologies; and 3) "back of the eye" retinal diseases, which include dry age-related macular degeneration, neovascular age-related macular degeneration, diabetic retinopathy, retinal vascular diseases (e.g. retinal vein occlusion, retinal artery occlusion), and retinal degenerations and dystrophies, in a subject, the method comprising administering an effective amount of the compound of any of Statements 1-9 to the subject such that the ophthalmic disease is treated.

Statement 20. A method of treating a frontal or distal eye indication in a subject, the method comprising administering an effective amount of the compound of any of Statements 1-9 to the subject such that the indication is treated.

Statement 21. A method of treating cancer in a subject, the method comprising administering an effective amount of the compound of any of Statements 1-9 to the subject such that the cancer is treated.

Statement 22. A method of treating an appetite disease in a subject, the method comprising administering an effective amount of the compound of any of Statements 1-9 to the subject such that the appetite disease is treated.

Statement 23. A method of treating systemic inflammatory or autoimmune diseases, such as graft versus host disease, sarcoidosis, systemic lupus erythematosus, others, in a subject, the method comprising administering an effective amount of the compound of any of Statements 1-9 to the subject such that the systemic inflammatory disease is treated.

Statement 24. A compound having the Formula (XX):

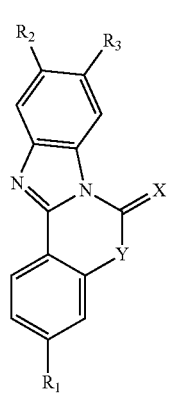

(XX)

or a pharmaceutically acceptable salt, solvate, hydrate, or derivative thereof, wherein X is oxygen (O) or sulfur (S); wherein Y is $NR_4$, or $CR_5R_6$; wherein $R_1$ is —$CH_2COOH$, —COOH, —$CH_2COOCR_7$, —$COOR_7$; —$CH_2CONH_2$, —$CONH_2$, —$CH_2CONR_5R_6$, or —$CONR_5R_6$; wherein each $R_2$ and $R_3$ are independently hydrogen (H), C1-C10 alkyl, —$OR_7$, —$OCH_2CH_2OR_7$, —$OCH_2CH_2NR_5R_6$, —$OCH_2CH_2COOR_7$ or —$OCH_2CH_2PO_3H$;

wherein $R_4$ hydrogen (H), C1-C10 alkyl, —$CH_2CN$, —$CH_2C(O)NH_2$, —$CH_2COOH$, —$CH_2SO_2CH_3$, —$CH_2CH_2NH_2$, —$CH_2CH_2OH$, —$CH_2$thienyl, —$CH_2$furanyl, —$CH_2CH_2$heterocycle, —$CH_2CH_2$cycloalkyl, —$CH_2CH_2$heterocycloalkyl, —$CH_2CHOCH_2OH$ or —$(CH_2)_nZ(CH_2)_mCH_3$, where n is an integer from 1 to 5, m is an integer from 0 to 5, and Z is oxygen (O) or sulfur (S);

wherein each $R_5$ and $R_6$ are independently hydrogen (H), C1-C5 alkyl, or $R_5$ and $R_6$ together may a 3 to 7-member cycloalkyl ring; and wherein $R_7$ is C1-C5 alkyl.

Statement 25. The compound of Statement 24, wherein X is oxygen.

Statement 26. The compound of any of Statement 24 or 25, wherein Y is NH, $NCH_3$, $NCH_2CH_3$, $NCH(CH_3)_2$

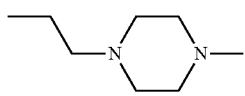

or, —$CH_2CH_2CH_2SCH_3$.

Statement 27. The compound of any of Statement 24-26, wherein $R_1$ is COOH.

Statement 28. The compound of any of Statement 24-27, wherein $R_2$ or $R_3$ is —$OCH_3$.

Statement 29. The compound of any of Statement 24-28, wherein $R_2$ and $R_3$ are —$OCH_3$.

Statement 30. A compound having the Formula (XXI):

(XXI)

or a pharmaceutically acceptable salt, solvate, hydrate, or derivative thereof, wherein X is oxygen (O) or sulfur (S); wherein $R_1$ is —$CH_2COOH$, —COOH, —$CH_2COOCR_7$, —$COOR_7$; —$CH_2CONH_2$, —$CONH_2$, —$CH_2CONR_5R_6$, or —$CONR_5R_6$; wherein each $R_2$ and $R_3$ are independently hydrogen (H), C1-C10 alkyl, —$OR_7$, —$OCH_2CH_2OR_7$, —$OCH_2CH_2NR_5R_6$, —$OCH_2CH_2COOR_7$ or —$OCH_2CH_2PO_3H$;

wherein each $R_5$ and $R_6$ are independently hydrogen (H), C1-C5 alkyl, or $R_5$ and $R_6$ together may a 3 to 7-member cycloalkyl ring; wherein $R_7$ is C1-C5 alkyl; and wherein w is 1 or 2.

Statement 31. The compound of Statement 30, wherein X is oxygen.

Statement 32. The compound of any of Statement 30-31, wherein $R_1$ is COOH.

Statement 33. The compound of any of Statement 30-32, wherein $R_2$ or $R_3$ is —$OCH_3$.

Statement 34. The compound of any of Statement 30-33, wherein $R_2$ and $R_3$ are —$OCH_3$.

Statement 35. A method of modulating CaMKK2 in a subject, the method comprising administering to the subject an effective amount of the compound of any of Statements 24-29.

Statement 36. A method of modulating CaMKK2 in a subject, the method comprising administering to the subject an effective amount of the compound of any of Statements 30-34.

Statement 37. A method of treating a frontal or distal eye indication in a subject, the method comprising administering an effective amount of the compound of any of Statements 24-29 to the subject.

Statement 38. A method of treating a frontal or distal eye indication in a subject, the method comprising administering an effective amount of the compound of any of Statements 30-34 to the subject.

Statement 39. A method of treating cancer in a subject, the method comprising administering an effective amount of the compound of any of Statements 24-29 to the subject.

Statement 40. A method of treating cancer in a subject, the method comprising administering an effective amount of the compound of any of Statements 30-34 to the subject.

Statement 41. A method of treating an appetite disease in a subject, the method comprising administering an effective amount of the compound of any of Statements 24-29 to the subject.

Statement 42. A method of treating an appetite disease in a subject, the method comprising administering an effective amount of the compound of any of Statements 30-34 to the subject.

Statement 43. A method of treating systemic inflammatory or autoimmune diseases, such as graft versus host disease, sarcoidosis, systemic lupus erythematosus, others, in a subject, the method comprising administering an effective amount of the compound of any of Statements 24-29 to the subject.

Statement 44. A method of treating systemic inflammatory or autoimmune diseases, such as graft versus host disease, sarcoidosis, systemic lupus erythematosus, others, in a subject, the method comprising administering an effective amount of the compound of any of Statements 30-34 to the subject.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A compound having the Formula (XX):

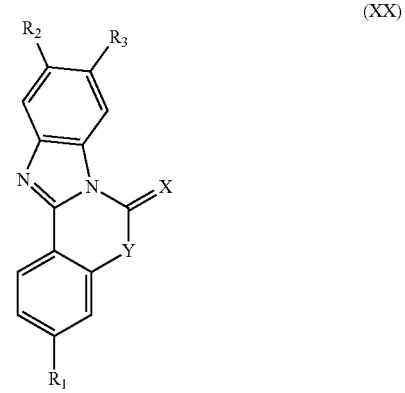

or a pharmaceutically acceptable salt, solvate, or hydrate thereof,
wherein X is oxygen (O);
wherein Y is $NR_4$;
wherein $R_1$ is —$CH_2COOH$, —COOH, —$CH_2COOCR_7$, —$COOR_7$; —$CH_2CONH_2$, —$CONH_2$, —$CH_2CONR_5R_6$, or —$CONR_5R_6$;
wherein each $R_2$ and $R_3$ are independently hydrogen (H), C1-C10 alkyl, —$OR_7$, —$OCH_2CH_2OR_7$, —$OCH_2CH_2NR_5R_6$, —$OCH_2CH_2COOR_7$ or —$OCH_2CH_2PO_3H$;
wherein $R_4$ hydrogen (H), C1-C10 alkyl, —$CH_2CN$, —$CH_2C(O)NH_2$, —$CH_2COOH$, —$CH_2SO_2CH_3$, —$CH_2CH_2NH_2$, —$CH_2CH_2OH$, —$CH_2$thienyl, —$CH_2$furanyl, —$CH_2CH_2$heterocycle, —$CH_2CH_2$cycloalkyl, —$CH_2CH_2$heterocycloalkyl, —$CH_2CHOCH_2OH$ or —$(CH_2)_nZ(CH_2)_mCH_3$, where n is an integer from 1 to 5, m is an integer from 0 to 5, and Z is oxygen (O) or sulfur(S);
wherein each $R_5$ and $R_6$ are independently hydrogen (H), C1-C5 alkyl, or $R_5$ and $R_6$ together may a 3 to 7-member cycloalkyl ring; and
wherein $R_7$ is C1-C5 alkyl.

2. The compound of claim 1, wherein $R_4$ is hydrogen (H), $C_1$-$C_{10}$ alkyl, —$CH_2CH_2$heterocycloalkyl, —$CH_2CHOCH_2OH$ or —$(CH_2)_nZ(CH_2)_mCH_3$.

3. The compound of claim 1, wherein Y is NH, $NCH_3$, $NCH_2CH_3$, $NCH_2CH_2F$, $NCH(CH_3)_2$, $NCH_2CH_2OCH_3$, $NCH_2CH_2CH_2SCH_3$, or

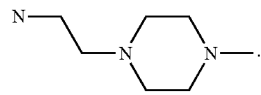

4. The compound of claim 1, wherein $R_1$ is COOH.
5. The compound of claim 1, wherein $R_2$ or $R_3$ is —$OCH_3$.
6. The compound of claim 1, wherein $R_2$ and $R_3$ are —$OCH_3$.
7. The compound of claim 1, wherein $R_4$ is hydrogen (H).
8. The compound of claim 1, wherein $R_4$ is $C_1$-$C_{10}$ alkyl.
9. The compound of claim 1, wherein $R_4$ is —$CH_2CH_2$heterocycloalkyl.
10. The compound of claim 1, wherein $R_4$ is —$CH_2CHOCH_2OH$.

11. The compound of claim 1, wherein $R_4$ is —$(CH_2)_nZ(CH_2)_mCH_3$.
12. The compound of claim 1, wherein Y is NH.
13. The compound of claim 1, wherein Y is $NCH_3$.
14. The compound of claim 1, wherein Y is $NCH_2CH_2F$.
15. The compound of claim 1, wherein Y is $NCH(CH_3)_2$.
16. The compound of claim 1, wherein Y is $NCH_2CH_2OCH_3$.
17. The compound of claim 1, wherein Y is $NCH_2CH_2CH_2SCH_3$.
18. The compound of claim 1, wherein Y is
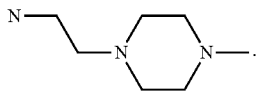
* * * * *